US005496960A

United States Patent [19]
Piers et al.

[11] Patent Number: 5,496,960
[45] Date of Patent: Mar. 5, 1996

[54] PROCESS FOR PRODUCTION OF BIS-(PENTAFLUOROPHENYL) BORANE AND USE THEREOF FOR PRODUCITION OF BASE FREE ZWITTERIONIC HOMOGENEOUS ZIEGLER-NATTA OLEFIN POLYMERIZATION CATALYSTS

[75] Inventors: Warren E. Piers; Rupert E. von Haken Spence, both of Guelph, Canada

[73] Assignee: University of Guelph, Ontario, Canada

[21] Appl. No.: 375,692

[22] Filed: Jan. 20, 1995

[30] Foreign Application Priority Data

Nov. 23, 1994 [GB] United Kingdom ............... 9423606

[51] Int. Cl.$^6$ ............... C07F 5/02; C07F 19/00; C07F 17/00; C07F 7/00
[52] U.S. Cl. ............... 556/8; 556/7; 568/1; 568/3
[58] Field of Search ............... 556/7, 8; 568/3, 568/1

[56] References Cited

PUBLICATIONS

Cationic D°/F° Metallocene Catalysts. Properties of Binuclear Organoborane Lewis Acid Cocatalysts and Weakly Coordinating Counteranions Derived Therefrom; Li Jiam, Einmin Yang, Charlotte Stern and Tobin J. Marks; Department of Chemistry, Northwestern University, Evanston, Illinois 60208–3113; Received May 31, 1994; Organometallics 1994, 13, 3755–3757.

Journal of Organometallic Chemistry, 156 (1978) 101–110; Elsevier Sequoia S. A., Lausanne–Printed in the Netherlands; Dipenylborane. A New Hydroborating Agent. Synthesis of Alkyldiphenylboranes and Their Application to the Conjugate Addition Reaction of Organoboranes; Peyton Jacob, III, Richard B. Wetherill Laboratory, Purdue University, West Lafayette, Indiana 47907 (U.S.A.) (Received Jan. 17th, 1978).

Primary Examiner—Porfirio Nazario-Gonzales
Attorney, Agent, or Firm—Lynn C. Schumacher; Dowell & Dowell

[57] ABSTRACT

There is disclosed a new boron-containing compounds such as bis-(pentafluorophenyl)borane, $(C_6F_5)_2BH$ and related compounds and a method for producing the compounds. The new borane is suitable for use as a hydroboration reagent for the rapid hydroboration of alkenes and alkynes. The borane is also suitable for use as a hydroboration reagent to produce useful boron reagents that can be used in Ziegler-Natta homogeneous olefin polymerization catalyst systems. Specifically, the borane reagent can be used to produce $Cp_2Zr\{\eta^3\text{-}CH(C_6H_5)[\ (\mu\text{-}H)B(C_6F_5)_2]\}$, which exhibits an efficacy for polymerization of ethylene.

19 Claims, 25 Drawing Sheets

SCHEME 1. SYNTHESIS OF $(C_6F_5)_2BH$, 1.

SCHEME 2

SCHEME 3

SCHEME 4

SCHEME 5

1

PROCESS FOR PRODUCTION OF BIS-(PENTAFLUOROPHENYL) BORANE AND USE THEREOF FOR PRODUCITION OF BASE FREE ZWITTERIONIC HOMOGENEOUS ZIEGLER-NATTA OLEFIN POLYMERIZATION CATALYSTS

FIELD OF THE INVENTION

The present invention relates to new borane reagents, bis(pentafluorophenyl)borane, $(C_6F_5)_2BH$ and related compounds and to methods for producing the reagents. The invention also relates to use of the new borane for the hydroboration of alkenes and alkynes and for producing new polymerization catalysts for polyethylene production.

BACKGROUND OF THE INVENTION

Boron reagents have long been known to have many applications in organic chemistry. Hydroboration is one of the most widely used organometallic reactions in organic synthesis and a wide variety of borane reagents have been produced which are tailored to many specific applications, as disclosed, for example, in K. Smith and A. Pelter, *Comprehensive Organic Synthesis,* Vol 8, (eds: B. M. Trost and I. Fleming) Pergamon Press, New York, 1991, p. 703. Hydroboration reactions are particularly useful for the conversion of alkenes and alkynes to alcohols or ketones. Generally, hydroboration simply involves the combination of an alkyne or an alkene (olefin) with a borane reagent in an appropriate solvent. One of the best known hydroborating reagents is 9-BBN (9-borabicyclo[3.3.1]-nonane) which is commercially available as a solid or as a solution in various solvents. A drawback to hydroboration of organics by reaction with 9-BBN is that they typically take several hours to go to completion.

Boron reagents have also been used as co-catalysts in catalyst systems used in the preparation of polymers such as polyethylene, a compound of major commercial importance, see X. Yang, C. L. Stern and T. J. Marks, *J. Am. Chem. Soc.,* Vol 116, p. 10015, 1994. Polyethylene is a very versatile plastic used in a wide variety of industrially useful products including plastic containers, toys and saran wrap, to mention just a few. The physical properties of this plastic are highly dependent on the chemical structure of the polymer comprising polyethylene, which in turn is strongly influenced by the chemical structure of the homogeneous catalysts used in the polymerization catalysts with the olefin monomers which are reacted to form the polymer chains.

Typically, the polymerization catalyst systems are comprised of two components including a catalyst precursor and a co-catalyst which, when combined, form the species responsible for joining the olefin monomers into the long chain polymers. One of the components is a group 4-based metallocene chloride or alkyl complex, and the other is a Lewis acid co-catalyst which serves to activate the metallocene to form the active species. Specifically, combinations of group 4-based bent metallocene compounds with group 13 Lewis acids often results in catalysts capable of polymerizing olefinic substrates by ring opening metathesis, as disclosed in Grubbs, R. H. and Tumas, W., *Science,* Vol. 243, p.907, 1989; or by Ziegler-Natta type mechanisms as disclosed in Sinn, H. and Kaminsky, W., *Adv. Organomet Chem,* Vol. 18, p. 99, 1992.

The architecture and chemical structure of the supporting ligand for the group 4 metal influences rates of initiation, propagation and termination, as well as the regio and steriochemistry of propagation when α-olefins are polymerized. Consequently, the steric and electronic properties of the ligand framework are crucial in determining the properties of the product of the polymerization reaction. As a result, the design of new polymerization catalysts is a very active field with the goal being to produce polymerization catalysts for producing plastics with superior properties.

Therefore there has been a need for a single polymerization catalyst which incorporates the catalyst precursor and the co-catalyst into a single molecule. While this goal of combining the components of the polymerization catalyst into a single molecule has been pursued, to date such attempts have been unsuccessful due to the synthesis problems involved in producing such a molecular species. The most significant challenge arises because of the need to incorporate the co-catalyst moiety at the latest possible stage in the catalyst synthesis. Hydroboration offers a synthetic solution to this challenge, but prior to the present invention suitable hydroboration reagents have not been known.

Combining all of the features required in an ethylene polymerization catalyst system into a single molecule would be advantageous because the catalyst should be "self-activating" and form a zwitterionic active species and be more soluble.

SUMMARY OF THE INVENTION

The present invention provides new boron containing compounds having the general formula $[(C_6R_5)_2BH]_n$ wherein n is selected from the group consisting of 1 and 2 and R is selected from the group consisting of fluorine (F), hydrogen (H), (trifluoromethyl) ($CF_3$) groups, and combinations thereof but not consisting entirely of H. In this aspect of the invention a new boron containing reagent $(C_6F_5)_2BH$ is specifically provided.

The invention provides a method of producing $[(C_6F_5)_2BH]_n$ comprising the steps of providing an amount of $ClB(C_6F_5)_2$ and mixing the $ClB(C_6F_5)_2$ with a source of hydride in a temperature range from about $-78°$ C. to about room temperature to produce a solution in which a precipitate comprising $[(C_6F_5)_2BH]_n$ is formed. The $[(C_6F_5)_2BH]_n$ is isolated from the solution.

In another aspect there is provided a method of hydroborating alkenes by reaction with $(C_6F_5)_2BH$, comprising providing a quantity of $[(C_6F_5)_2BH]_2$ and a quantity of a suitable alkene and mixing said quantity of $[(C_6F_5)_2BH]_2$ with a suitable dry organic solvent to produce a suspension comprising $(C_6F_5)_2BH$ and mixing therewith said quantity of said suitable alkene, wherein said $(C_6F_5)_2BH$ is present in an amount effective to cause said quantity of suitable alkene to undergo hydroboration.

A method of hydroborating alkynes by reaction with $(C_6F_5)_2BH$ is provided and comprises the steps of providing a quantity of $[(C_6F_5)_2BH]_2$ and a quantity of a suitable alkyne and mixing said quantity of $[(C_6F_5)_2BH]_2$ with a suitable dry organic solvent to produce a suspension comprising $(C_6F_5)_2BH$ and mixing therewith said quantity of said alkyne, wherein said $(C_6F_5)_2BH$ is present in an amount effective to cause said quantity of alkyne to undergo hydroboration.

In another aspect of the invention a compound having the formula $Cp_2Zr\{R'''[(\mu\text{-}H)B(C_6F_5)_2]\}$ is provided wherein Cp is cyclopentadienyl and R''' is selected from the group consisting of $CH_2$ and $(\Theta^3\text{-}CH(C_6H_5))$.

The invention also provides a method of producing chelating bis borane co-catalysts by hydroboration of terminal alkynes by reaction with $(C_6F_5)_2BH$. The method comprises providing an amount of a terminal alkyne having a formula $RC\equiv CH$ wherein R is selected from the group consisting of tertiary butyl, and phenyl and alkyl organic functional groups. The method includes reacting the terminal alkyne with an effective amount of $(C_6F_5)_2BH$ to cause the terminal alkyne to undergo hydroboration to produce chelating bis borane co-catalysts having a formula $RCH_2CH[B(C_6F_5)_2]_2$.

BRIEF DESCRIPTION OF THE DRAWINGS

The invention will now be described, by example only, reference being had to the accompanying drawings, in which.

BRIEF DESCRIPTION OF THE TABLES

Table 1 summarizes the hydroboration reactions of simple alkenes and alkynes using Bis-(pentafluorophenyl)borane.

DETAILED DESCRIPTION OF THE PREFERRED EMBODIMENT

A) Synthesis and Characterization of Bis-(pentafluorophenyl)borane

Hydroboration is one of the most widely used organometallic reactions in organic synthesis. The inventors considered that a boron containing molecule with the formula $(C_6F_5)_2BH$ would be very reactive and highly electrophilic. Hydroboration of olefin or alkyne functionalities dangling from the supporting ligand structure of a homogeneous Ziegler-Natta catalyst precursor would incorporate a pendant $B(C_6F_5)_2$ moiety potent enough to activate the catalyst precursor via intramolecular abstraction of an alkyl group from the zirconium center. Model studies revealed this borane to be an exceptionally active hydroboration reagent.

Figure 1:
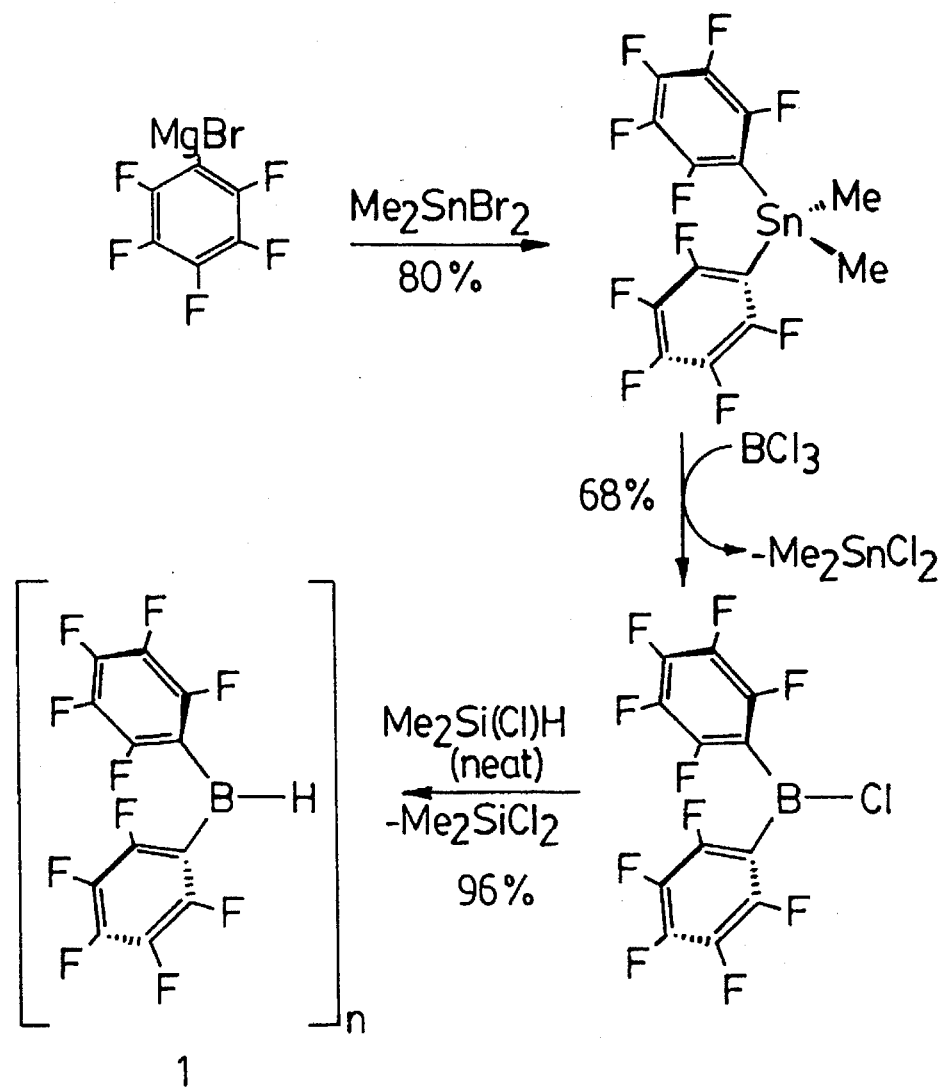
FIG. 1 illustrates a reaction scheme (scheme I) used to produce Bis-(pentafluorophenyl)borane, $[(C_6F_5)_2BH]_n$.

Referring to FIG. 1, Bis-(pentafluorophenyl)borane, $[(C_6F_5)_2BH]_n$, 1, was prepared from the known chloroborane $ClB(C_6F_5)_2$ (as disclosed in R. D. Chambers, T. Chivers, J. Chem. Soc., p. 3933, 1965) in the absence of Lewis bases via reactions with hydride sources such as $[Cp_2Zr(Cl)H]_n$, $Bu_3SnH$ or $Me_2Si(Cl)H$ as shown in Scheme 1. Conventional metathetical methods for transformations of this type that are well known by those skilled in the art are not advisable, because they necessitate the use of donor solvents which are difficult to remove completely (if at all) due to the high Lewis acidity of 1. For example, tetrahydrofuran (THF) could not be removed from 1 and at 80° C. was observed to ring open THF to yield $(C_6F_5)_2BO(CH_2)_3CH_3$. The most convenient hydride transfer agent proved to be $Me_2Si(Cl)H$, because it also served as solvent for the reaction and the byproduct $Me_2SiCl_2$ was easily removed; 1 was observed to precipitate over the course of one hour and was isolated in high yield (96%) by filtration. The overall yield of 1 from bromopentafluorobenzene was 52%.

Experimental Procedures i) Bis(pentafluorophenyl)borane:

To an evacuated flask containing $ClB(C_6F_5)_2$ (7.00 g, 18.4 mmol) at −78° C. was condensed $ClHSiMe_2$ (10.2 g, 108 mmol). On warming the flask to room temperature, the $ClB(C_6F_5)_2$ was observed to dissolve and a new white precipitate was formed. The solution was stirred for 1 hour and then filtered to give 6.14 g (17.7 mmol, 96%) of the borane as a white crystalline powder.

The method disclosed herein for producing the borane reagent, $(C_6F_5)_2BH$, is advantageous because the reactant also serves as solvent, and is added in excess to dissolve the boron chloride, as well as converting the latter to the hydride. The by-products are easily removed under vacuum and the yield of 96% from borane chloride is exceptionally high. $(C_6F_5)_2BH$ may also be generated by treatment of the boron chloride with $ClHSiMe_2$, $[Cp_2Zr(Cl)H]_n$ or $Bu_3SnH$ in hexane or benzene. The reaction may also be carried out at room temperature or in the temperature range of $-78°$ C. to room temperature.

Those skilled in the art will understand that there are many sources of hydride which may be used. For example, the hydride source may be $R_3MH$ or $R_2ClMH$, in which R is an alkyl or aryl functional group, and M is Si, Ge or Sn. The hydride source could also be $Cp_2MH_2$ or $[Cp_2M(Cl)H]_n$, wherein Cp is cyclopentadienyl and M is Ti, Zr or Hf. Metal hydrides from Group 4 and Group 14 elements of the periodic table are also suitable hydride sources.

The products were characterized by $^1H$, $^{13}C\{^1H\}$, $^{19}F$(referenced to $CFCl_3$ at 0.0 ppm), and $^{11}B$ (referenced to $BF_3.Et_2O$ at 0.00 ppm) NMR spectroscopy. The $^{19}F$ NMR spectra generally showed that the ortho-fluorines of the pentafluorophenyl ring fell within the range $-130$ to $-133$ ppm, the para-fluorines fell between $-148$ to $-153$ ppm, and the meta-fluorines fell between $-162$ to $-164$ ppm. The $^{11}B$ NMR signals generally had a maximum between 58 to 78 ppm, typical of neutral, three coordinate boron.

Figure 2:
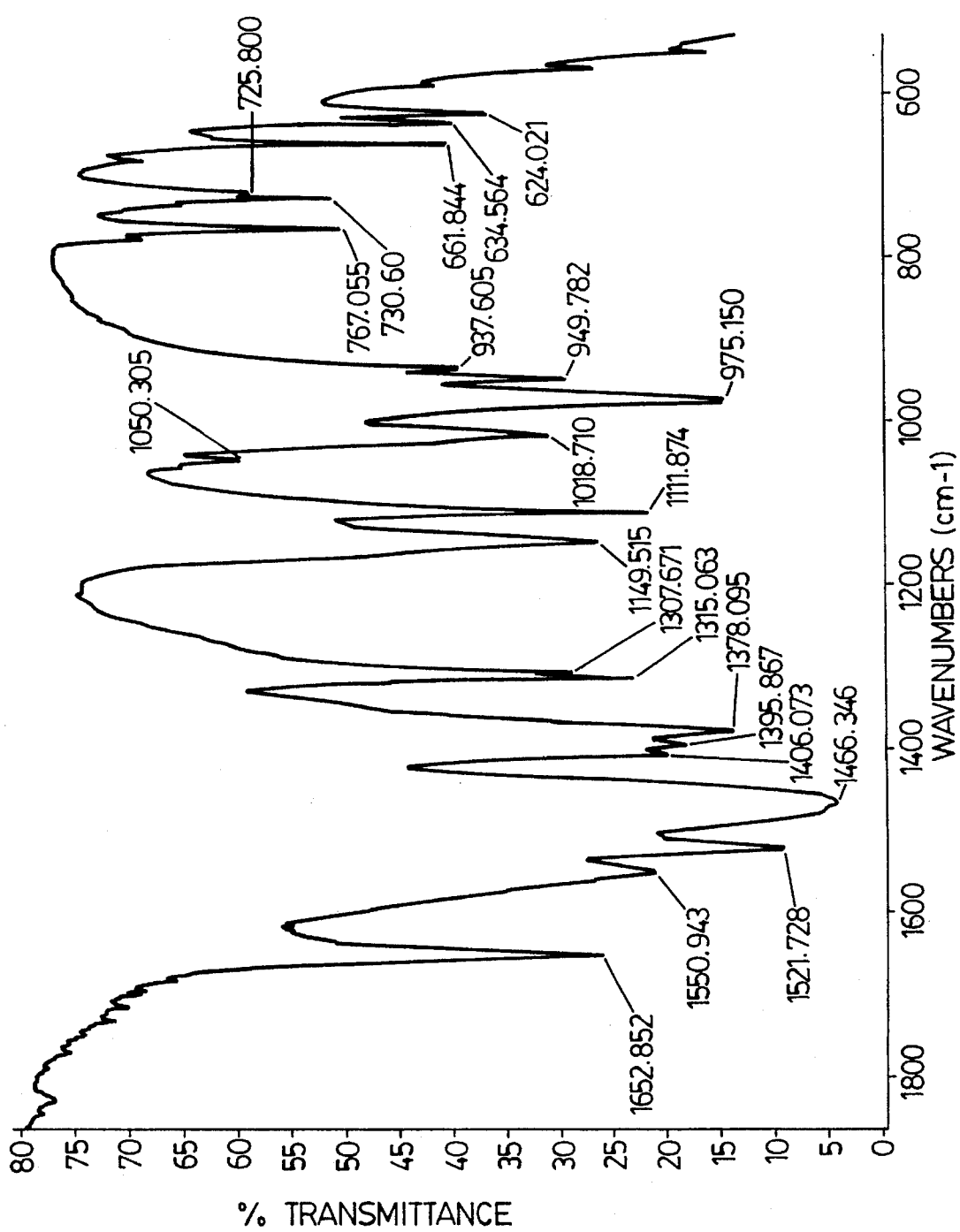
FIG. 2 shows the infrared spectrum of $[(C_6F_5)_2BH]_2$ as Nujol mull.
Figure 3:
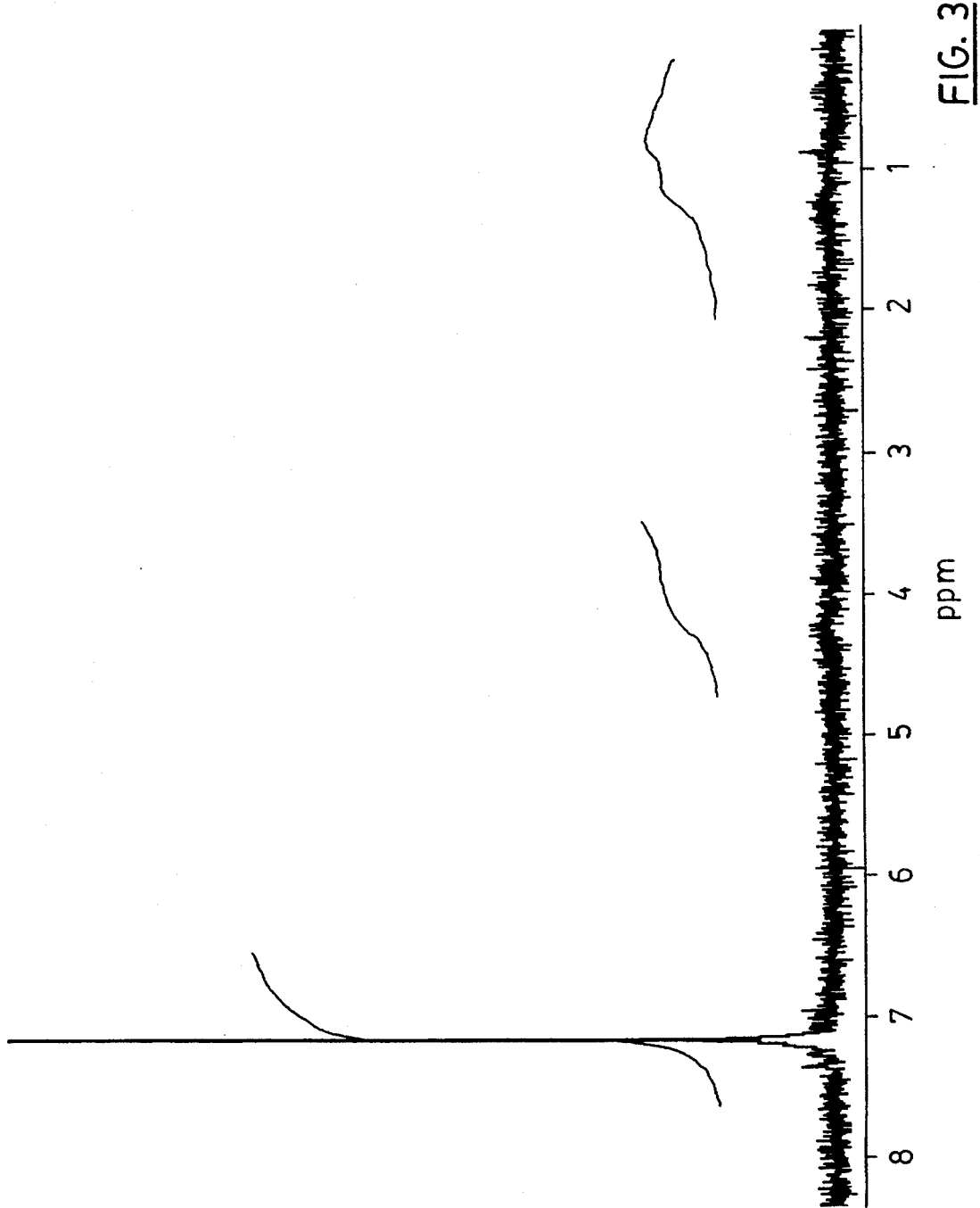
FIG. 3 shows the 400 MHz $^1H$ NMR spectrum of $[(C_6F_5)_2BH]_n$ in $C_6D_6$ solution.
Figure 4:
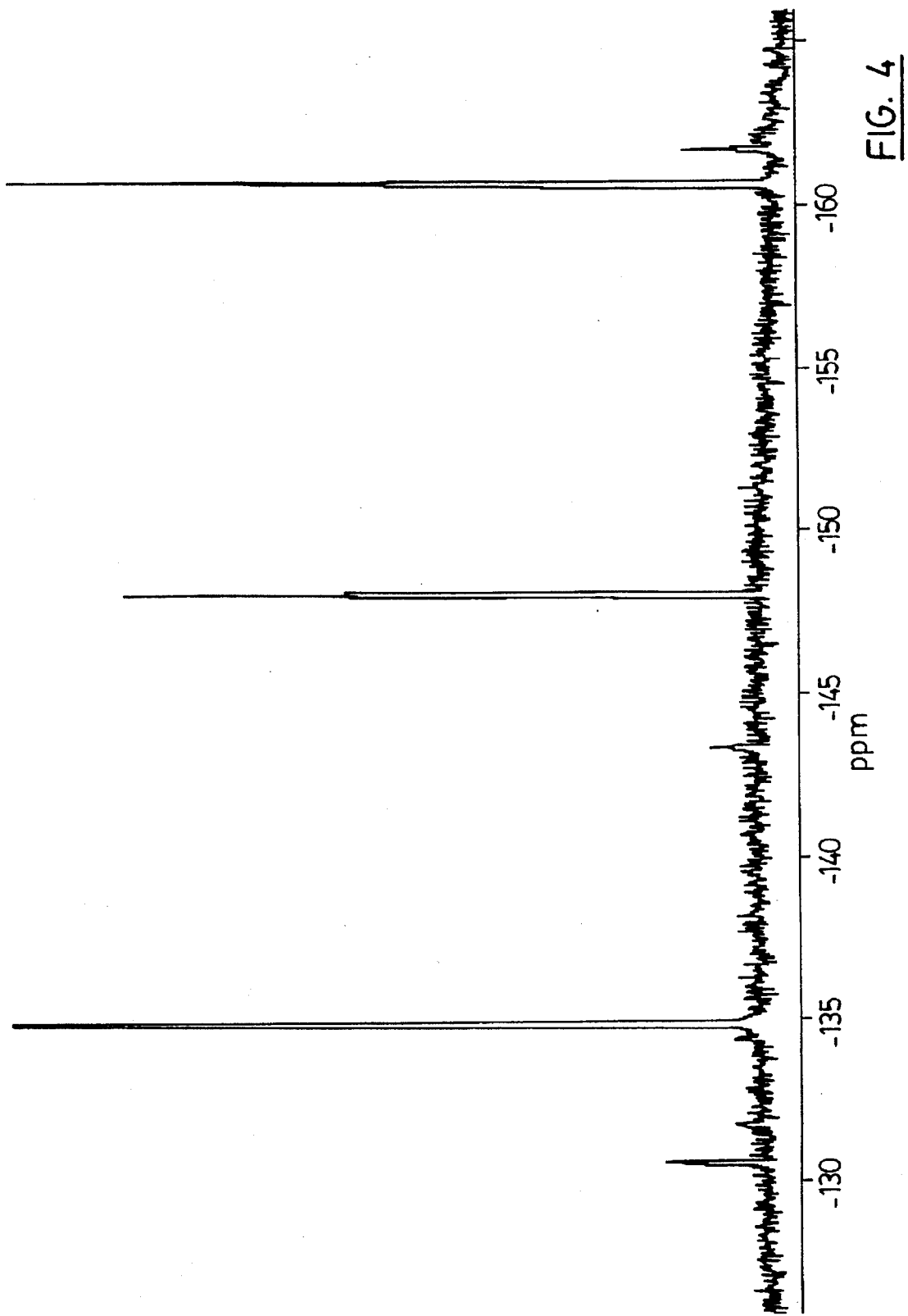
FIG. 4 shows the $^{19}F$ NMR spectrum of $[(C_6F_5)_2BH]_n$ in $C_6D_6$ solution.
Figure 5:
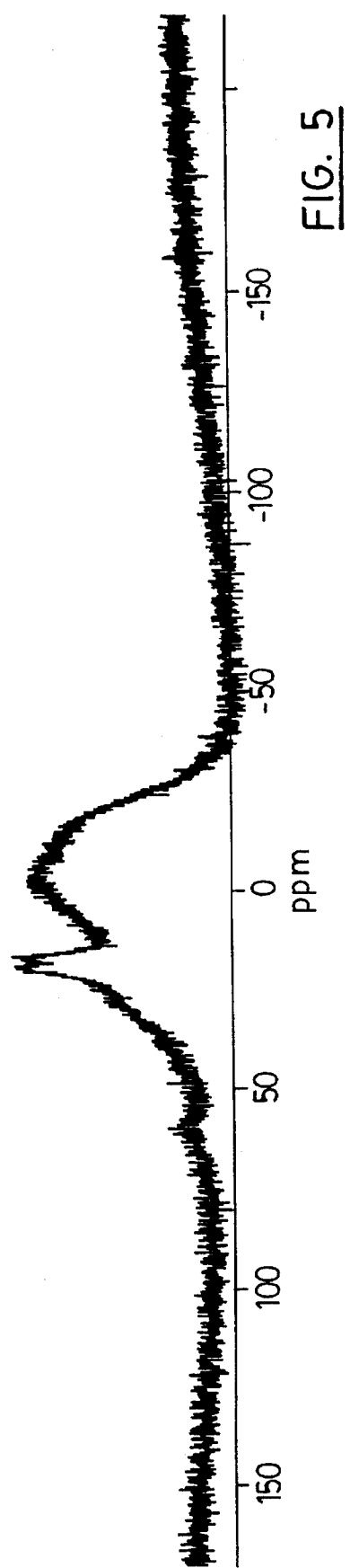
FIG. 5 shows the $^{11}B$ NMR spectrum of $[(C_6F_5)_2BH]_n$ in $C_6D_6$ solution.
Figure 6:
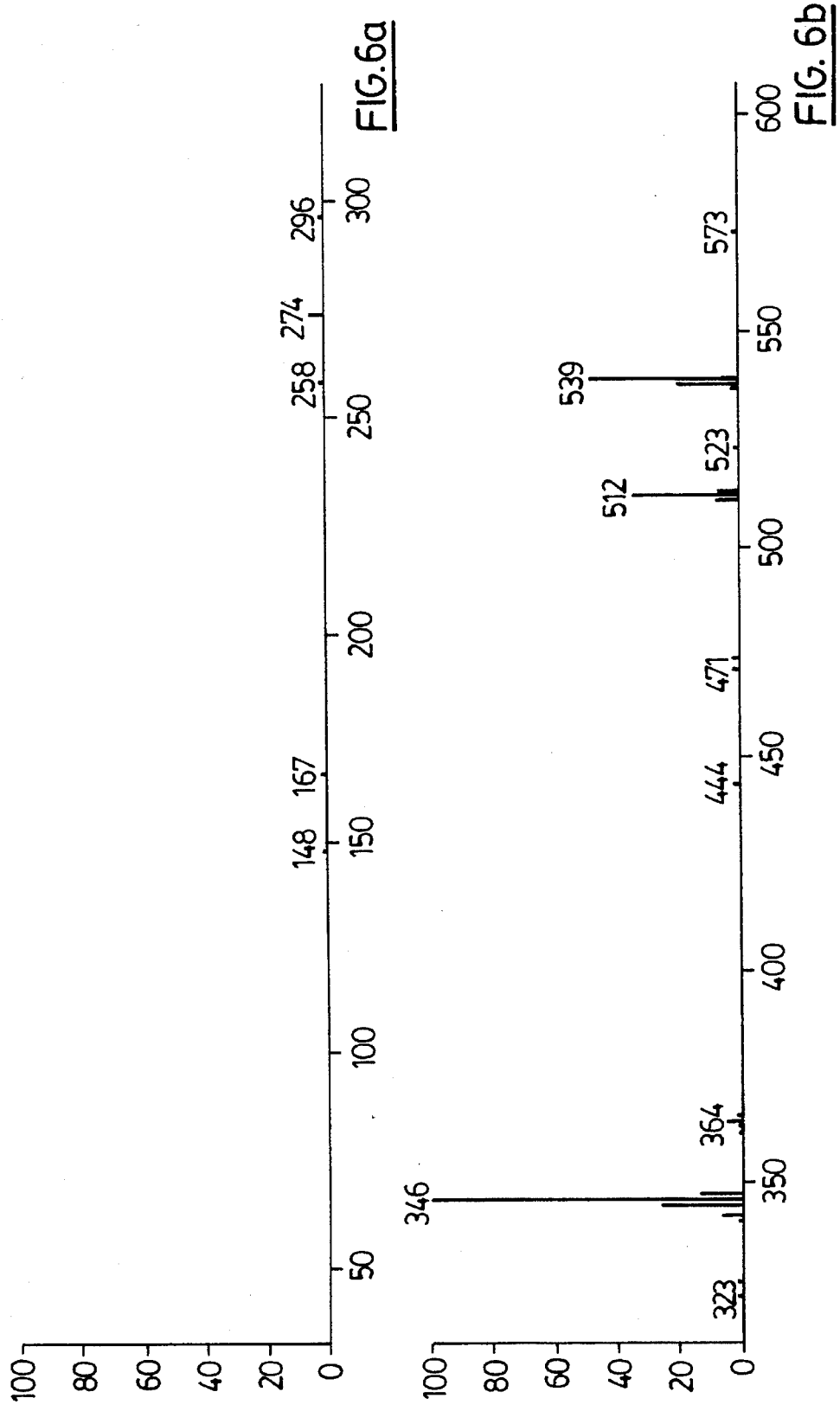
FIG. 6a shows the mass spectrum (70 eV) of $[(C_6F_5)_2BH]_n$ up to mass 300.
FIG. 6b shows the mass spectrum (70 eV) of $(C_6F_5)_2BH]_n$ from mass 300 to 400.

The infrared, NMR and mass spectroscopic (MS) results are illustrated in FIGS. 2 to 6. Distinguishing features of these spectra supporting the structure of $(C_6F_5)_2BH$ are as follows. FIG. 3: $^1H$ NMR ($C_6D_6$, ppm): 4.2 (br, whh ≈25 Hz). FIG. 5: $^{11}B$ NMR ($C_6D_6$, 25° C., ppm): major species, 18.0; minor species 60.1. FIG. 4: $^{19}F\{^1H\}$ NMR ($C_6D_6$, 10 mM, 25° C., ppm): major species (90%), $-134.8$ (2F), $-148.0$ (1F), $-160.7$ (2F); minor species (10%), $-130.5$ (2F); $-143.4$ (1F), $-161.7$ (2F). FIG. 2: IR (Nujol, NaCl): 1652 s, 1550 m (B-H), 1521 m, 1406 w, 1395 w, 1315 s, 1307 w, 1149 s, 1111 s, 1050 w, 1018 m, 975 s, 949 m, 937 w, 767 m, 661 m, 634 w, 624 w. MS (Cl,70 eV): m/z=346 (M$^+$). Anal. Calc'd for $C_{12}F_{10}BH$: C, 41.67; H, 0.29. Found: C, 41.87; H, 0.33.

Figure 7:
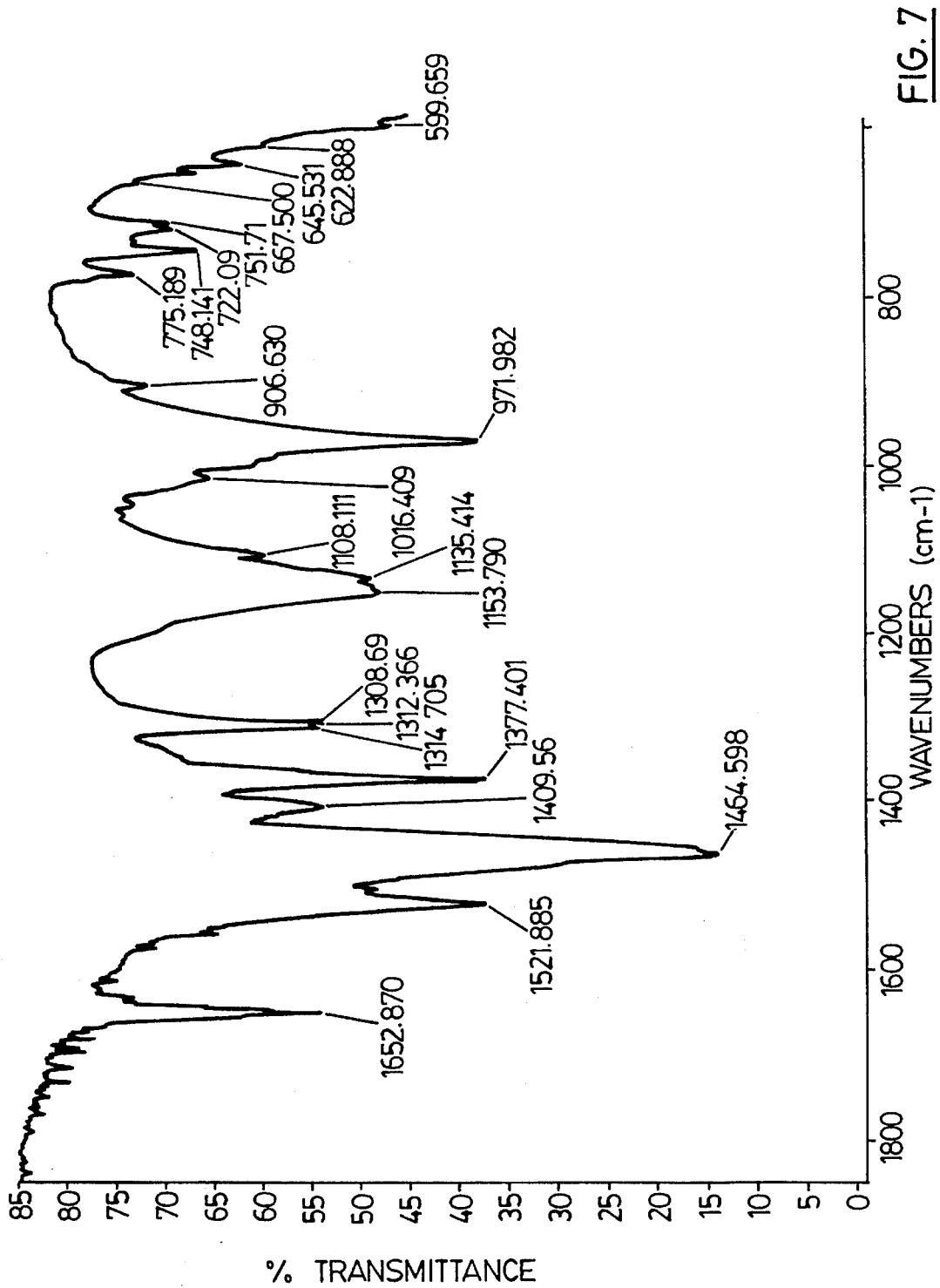
FIG. 7 shows the infrared spectrum of $[(C_6F_5)_2BH]_2$ as Nujol mull.
Figure 8:
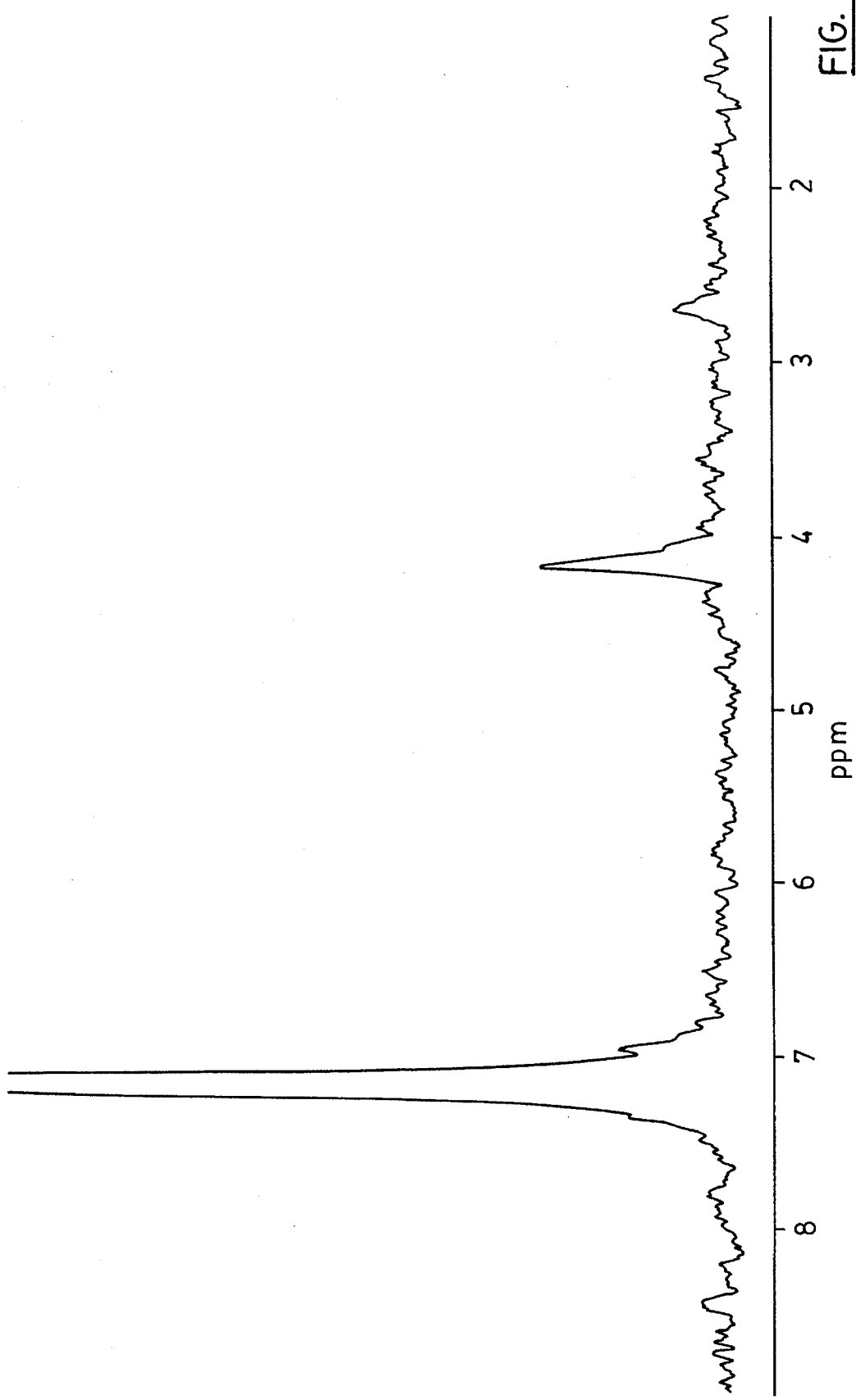
FIG. 8 shows the $^2H$ NMR spectrum of $[(C_6F_5)_2BH]_n$ in $C_6H_6$ solution.

Studies by the inventors of the crystal structure of the compound $ClB(C_6F_5)_2$ revealed the $C_6F_5$ rings are twisted ca. 30° out of the plane containing Cl, B and the two ipso aromatic carbons to avoid severe steric interaction between the ortho fluorine atoms on the two $C_6F_5$ rings. Molecular models of the borane, monomer and dimer show this twisting is required to avoid these steric interactions and so I exhibits a similar structure.

ii) Deutero-bis(pentafluorophenyl)borane:

$ClB(C_6F_5)_2$ (1.45 g, 3.8 mmol) was dissolved in hexane (6 mL) and a solution of tributyltin deuteride (1.11 g, 3.8 mmol) in hexane (2 mL) was added over a period of five minutes. This resulted in the immediate precipitation of $(C_6F_5)_2BD$ as a white solid. After 1 hour the solution was filtered and the solid washed with a small amount of cold hexane to achieve a yield 1.07 g, 3.1 mmol, 81%. The infrared and NMR results are summarized in FIGS. 7 and 8. $^2H\{^1H\}$ NMR ($C_6H_6$, ppm): 4.2 (br, whh=6 Hz).

iii) Characterization of Bis(pentafluorophenyl)borane:

Bis(pentaflourophenyl)borane 1 is a white, microcrystalline, oxygen and moisture sensitive solid which was found to be to stable (i.e., it retained its activity) for at least six months when stored under an inert atmosphere. Spectroscopic evidence indicated that the solid material exists as a dimer, $[(C_6F_5)_2BH]_2$. Thus, in FIG. 1, n can take on a value of 1 or 2 and in a suitable organic solvent both species are present due to the establishment of an equilibrium between the solid dimer form and the monomer. In hydroboration reactions using this borane the active species solution is the monomer but there is an equilibrium between the solid phase dimer and the monomer. Hereinafter, reference to 1 means the monomeric form only, $(C_6F_5)_2BH$ as this is the active species useful in the reactions disclosed below.

The infra-red spectrum of the solid represented in FIG. 2 shows a strong band characteristic of the $v_{asym}$ in phase mode for a B-(μ-H)$_2$-B unit at 1550 cm$^{-1}$, see G. Socrates, *Infrared Characteristic Group Frequencies*, Wiley; New York, p. 130, 1980, and no bands corresponding to terminal B-H stretches are present. Solution NMR data, were, however, consistent with the presence of monomeric $(C_6F_5)_2BH$. Most convincingly, the $^{11}B$ NMR spectrum (FIG. 5) revealed the presence of a minor species (≈10%) which resonated at 60.1 ppm in addition to a major signal at 18.0 ppm. The downfield resonance appears in the region associated with monomeric dialkyl boranes, see E. Negishi, J. J. Katz and H. C. Brown, *J. Am. Chem. Soc.*, Vol. 94, p. 4025, 1972, while the signal due to the major species is more typical of a dimeric borane as disclosed in J. A. Soderquist and H. C. Brown, *J. Org. Chem.*, Vol. 45, p. 3571, 1980. Thus, although a dimer in the solid state, dissociation into a monomeric borane is facile in aromatic solvents.

In addition to $(C_6F_5)_2BH$, other structurally similar boranes can be produced in accordance with the present invention. For example, those skilled in the art will appreciate that some of the fluorines F can be replaced by other halogens such as chlorine (Cl), iodine (I) and bromine (Br). However the resulting compounds may be environmentally problematic and exhibit catalytic properties less efficacious than $(C_6F_5)_2BH$ with the catalytic properties decreasing with each fluorine substitution.

Figure 9:
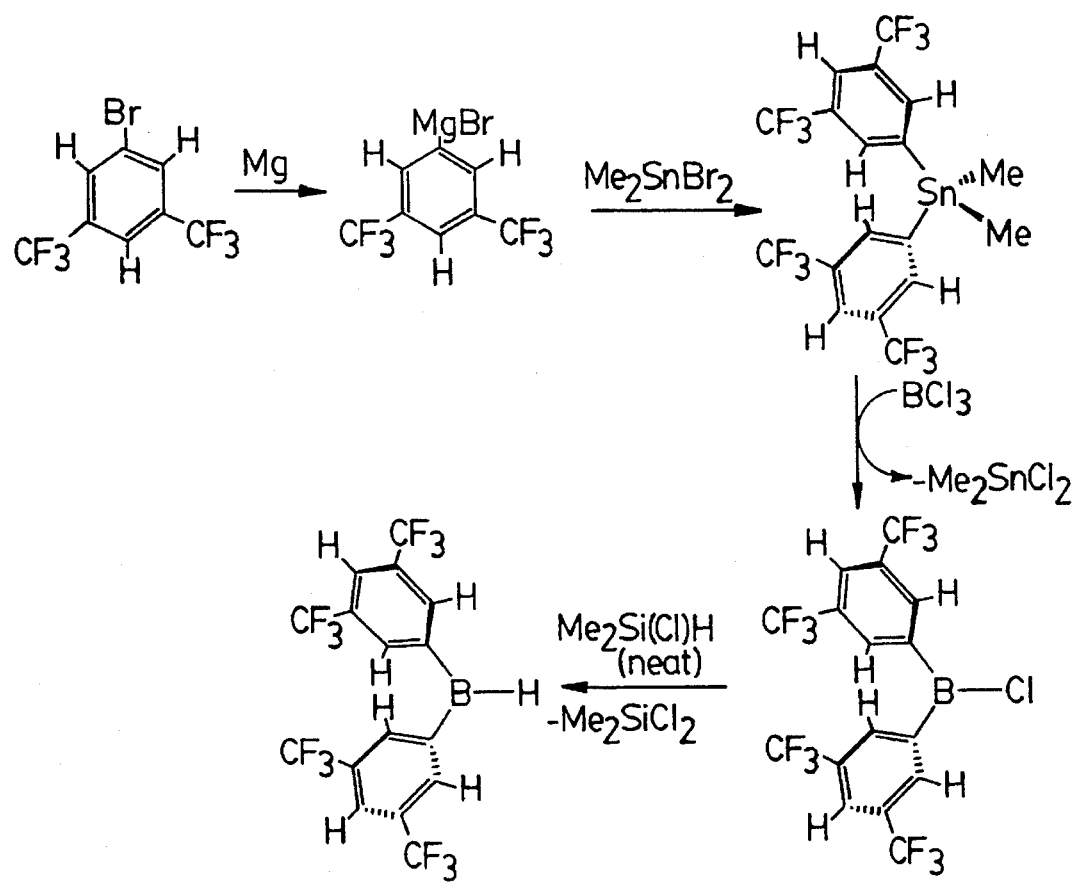
FIG. 9 illustrates the proposed reaction scheme (scheme II) used to produce $[3,5-(CF_3)_2C_6H_3]_2BH$ in accordance with the present invention.

Similarly, a borane reagent with 3,5-bis(trifluoromethyl)aryl groups would be produced according to scheme II in FIG. 9 and the aryl groups are expected to exhibit a similar catalytic efficacy observed with $(C_6F_5)_2BH$ since the aryl substituted group is almost as effective an electron withdrawing group as the fully fluorinated group. Thus, [3,5-$(CF_3)_2C_6H_3]_2BH$ is predicted by the inventors to exhibit nearly the same utility as $(C_6F_5)_2BH$ as a hydroboration reagent. Substitution of some of the fluorines for hydrogen would result in a lowering of the efficacy of this reagent as a hydroboration agent.

B) Utility of Bis-(pentafluorophenyl)borane i) Hydroboration of Alkenes and Alkynes Using Bis-(pentafluorophenyl)borane The inventors have determined that Bis-(pentafluorophenyl)borane is a highly active hydroboration reagent towards simple olefin (alkenes) and alkyne substrates. The general hydroboration procedure comprised adding to a suspension of $(C_6F_5)_2BH$ (0.1 mmol) in dry benzene (0.6 mL) under an argon atmosphere, a dried alkene or alkyne substrate (1 eq) via syringe. The mixture was sonicated for 30–60 seconds and then shaken, and the mixture was monitored by $^1H$ NMR spectroscopy.

In addition to dry benzene, dry methylene chloride and hexane may optionally be used as the solvent. In addition, it will be understood by those skilled in the art that other non-coordinating aromatic, hydrocarbon or halogenated solvents may be used as the organic solvent in which the hydroboration reaction takes place. The inventors have determined that coordinating solvents which act as Lewis acids, such as tetrahydrofuran (THF), sometimes inhibit hydroboration reactions. Therefore, coordinating solvents may be used in some, but not all, hydroboration reactions.

Table I lists several examples of the hydroboration of simple alkenes and alkynes using the borane reagent $(C_6F_5)_2BH$ in accordance with the present invention. Addition of the alkene or alkyne to a benzene suspension of the borane led to the rapid uptake of the solid, with the reaction being complete within two minutes. The reactions were all quantitative by NMR, and the products were characterized by $^1H$ and $^{13}C$ NMR spectroscopy or by further derivitization of the alkyl borane products. Even sterically demanding alkenes (entry 1) were hydroborated very rapidly and methylcyclohexene was hydroborated with no noticeable rate difference when compared to methylcyclopentene, see H. C. Brown, R. Liotta and C. G. Scouten, *J. Am. Chem. Soc.*, Vol. 98, p. 5297, 1976. Although relative rates of hydroboration for these two substrates may be quite different, in practical terms the rate difference is not important due the high activity of 1. These results favourably contrasted with those seen in reactions employing the common hydroboration reagent 9-BBN which, under identical conditions, took several hours to go to completion with these substrates.

The only substrates which did not react rapidly with 1 were those which had a $B(C_6F_5)_2$ functionality attached, i.e. those formed upon monohydroboration of alkynes (entries 6–8). In addition to being more sterically encumbered, the electron withdrawing effect of the $B(C_6F_5)_2$ substituent likely deactivates the alkene towards subsequent hydroboration. By comparison, hydroboration of alkynes with 9-BBN generally proceeded more rapidly for the second hydroboration, often precluded isolation of the singly hydroborated product unless excess substrate was employed, see H. C. Brown and C. G. Scouten and R. Liaotta, *J. Am. Chem. Soc.*, Vol 101, p. 96, 1979.

Alkenes with other strong electron withdrawing groups present will, as in the presence of $B(C_6F_5)_2$, undergo hydroboration slowly due to inhibition of the hydroboration reaction by the electron withdrawing groups. Therefore, it will be understood that suitable alkynes or alkenes which undergo hydroboration reactions are those lacking strong electron withdrawing functional groups.

Entries 2–4 in Table 1 illustrate that 1 hydroborated the substrates via the typical cis addition mechanism commonly accepted as being operative, see H. C. Brown, B.C. Subba Rao, *J. Am. Chem. Soc.*, Vol. 81, p. 6428, 1959. Regioselectivity was found to be excellent for substrates for which multiple products were possible. For example, styrene was hydroborated to the isomer shown with >98% selectivity (as shown by $^1H$ NMR spectroscopy and oxidation to 2-phenylethanol, vide infra). In some instances (entries 1–3) facile isomerization processes via a retrohydroboration-rehydroboration sequence were observed over the course of a few hours at room temperature. This behaviour is typical for the thexyl substituent as taught in E. Negishi and H. C. Brown, *Synthesis*, p. 153, 1980, but for other substrates elevated temperatures are usually required to induce these rearrangements, as disclosed in L. D. Field and S. P. Gallagher, *Tetrahedron Lett.*, Vol. 26, p. 6125, 1985. Advantageously, the differences in rates of initial hydroboration versus rearrangement in these systems allows for good control in obtaining either the kinetic or thermodynamic products.

Figure 10:
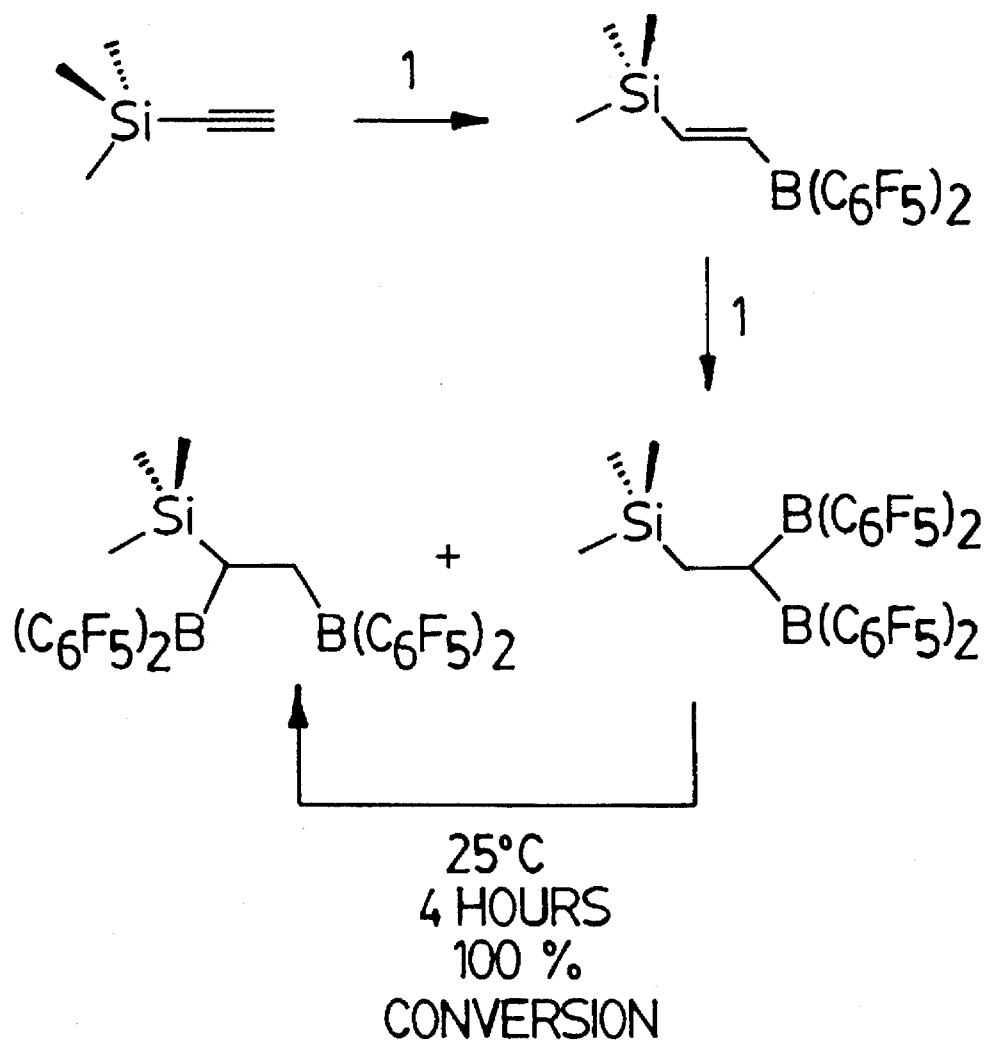
FIG. 10 shows a reaction scheme (scheme III) of the hydroboration of trimethylsilyl acetylene using $(C_6F_5)_2BH$.

Selective monohydroboration of terminal alkynes was effected by reaction of substrates with a single equivalent of 1 (Table I: entries 7 and 8). Although slower, double hydroboration occurred upon addition of a second equivalent of the borane. In the case of phenylacetylene, the product was the 1,1 isomer as shown in Table I, which is the normal selectivity observed with other borane reagents, see H. C. Brown and C. G. Scouten and R. Liaotta, *J. Am. Chem. Soc.*, Vol 101, p. 96, 1979. In contrast, the thermodynamic product for trimethylsilylacetylene was the 1,2 isomer. Initially, a mixture of the two possible products of double hydroboration was observed (ratio of 1,1:1,2= 2.5:1, see Scheme III shown in FIG. 10) which converted to the 1,2 regioisomer quantitatively.

A similar phenomenon was observed for vinyltrimethylsilane, (entry 9). The kinetic product in this reaction was that with the expected selectivity, i.e. 1-(trimethylsilyl)-2-bis(pentafluorophenyl)borylethane. Upon heating to 100° C., this compound isomerized to a mixture (ratio = 85:15) of the two possible regioisomers consisting primarily of the isomer with boron attached to the α carbon. Electronic preference for boron to occupy the α position in these silylated substrates was observed in the parent reactions with $BH_3$, i.e. when steric repulsions between the Me3Si group and boron substituents are at a minimum.

Figure 11:
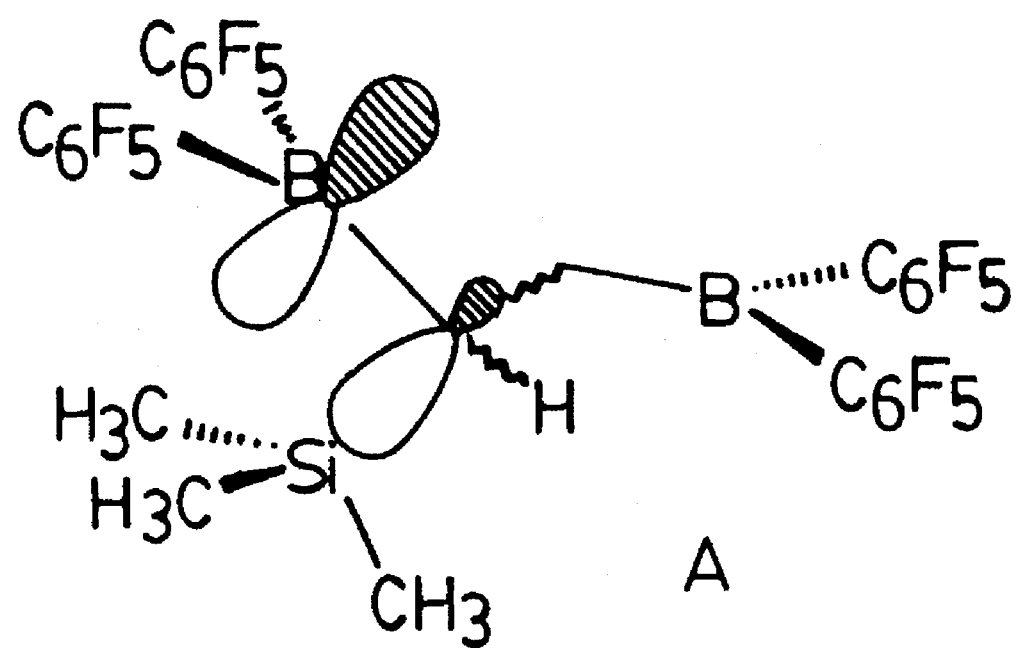
FIG. 11 illustrates the orbital interaction of the ground state of an intermediate complex formed between a silicon containing terminal alkyne and $(C_6F_5)_2BH$.

Similarly, hydroboration of substrates with the general formula $RC≡CSiMe_3$ show selectivity wherein boron is attached to the carbon α to silicon in the monohydroborated product, see J. A. Soderquist, J. C. Colberg and L. Del Valle, *J. Am. Chem. Soc.*, Vol. 111, p. 4873, 1989. These observations, and the results disclosed herein suggest that there is a thermodynamic preference for silicon to occupy a position 13 to a boron center in analogy to the well known "β-silicon effect" in the stabilization of carbocations, see J. B. Lambert, *Tetrahedron*, Vol. 46, p. 2677, 1990. Instead of stabilizing a carbocation-like transition state, the boron migrates to form a more stable ground state (A) shown in FIG. 11.

The inventors determined that oxidation of the hydroborated products, $RB(C_6F_5)_2$, could not be effected cleanly with aqueous methodology, or, with 3- chloroperoxybenzoic acid (MCPBA), due to the proteolytic instability of the $B(C_6F_5)_2$ group and to loss of $HC_6F_5$. The inventors have found that anhydrous $Me_3NO$ is a mild and efficient reagent for oxidizing the alkyl boranes to alcohols in high yields. For example 3,3-dimethyl-1-butanol was isolated in 58% yield (unoptimized) from the hydroboration of tert-butyl ethylene. Entries 7 and 8 in Table I are predicted by the inventors to be excellent chelating Lewis acid activators for a variety of organic reactions and Ziegler-Natta olefin polymerization systems.

It will be appreciated by those skilled in the art that alkenes and alkynes are not the only substrates which will undergo hydroboration using $(C_6F_5)_2BH$. A ketone, specifically acetone, has also been hydroborated using the new borane reagent disclosed herein.

Hydroboration of terminal alkynes having the formula RC≡CH in which R is selected from the group consisting of tertiary butyl, and phenyl and alkyl organic functional groups results in the production chelating bis borane cocatalysts.

ii) The Reactions of Bis-(Pentafluorophenyl)borane with Bis-Alkyl Zirconocenes

Figure 13:
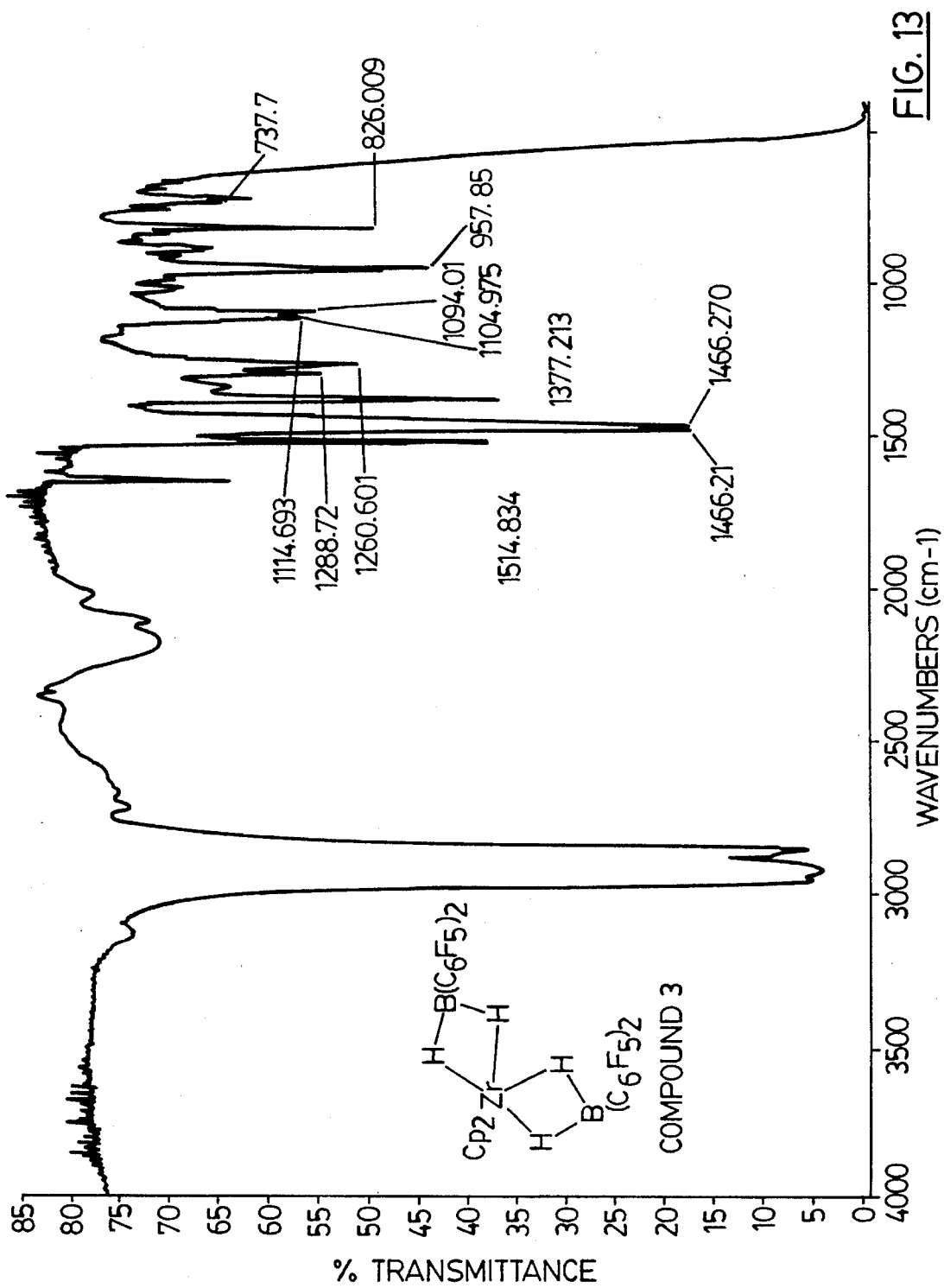
FIG. 13 shows the infrared spectrum of compound 3, as Nujol mull, described hereinafter.
Figure 14:
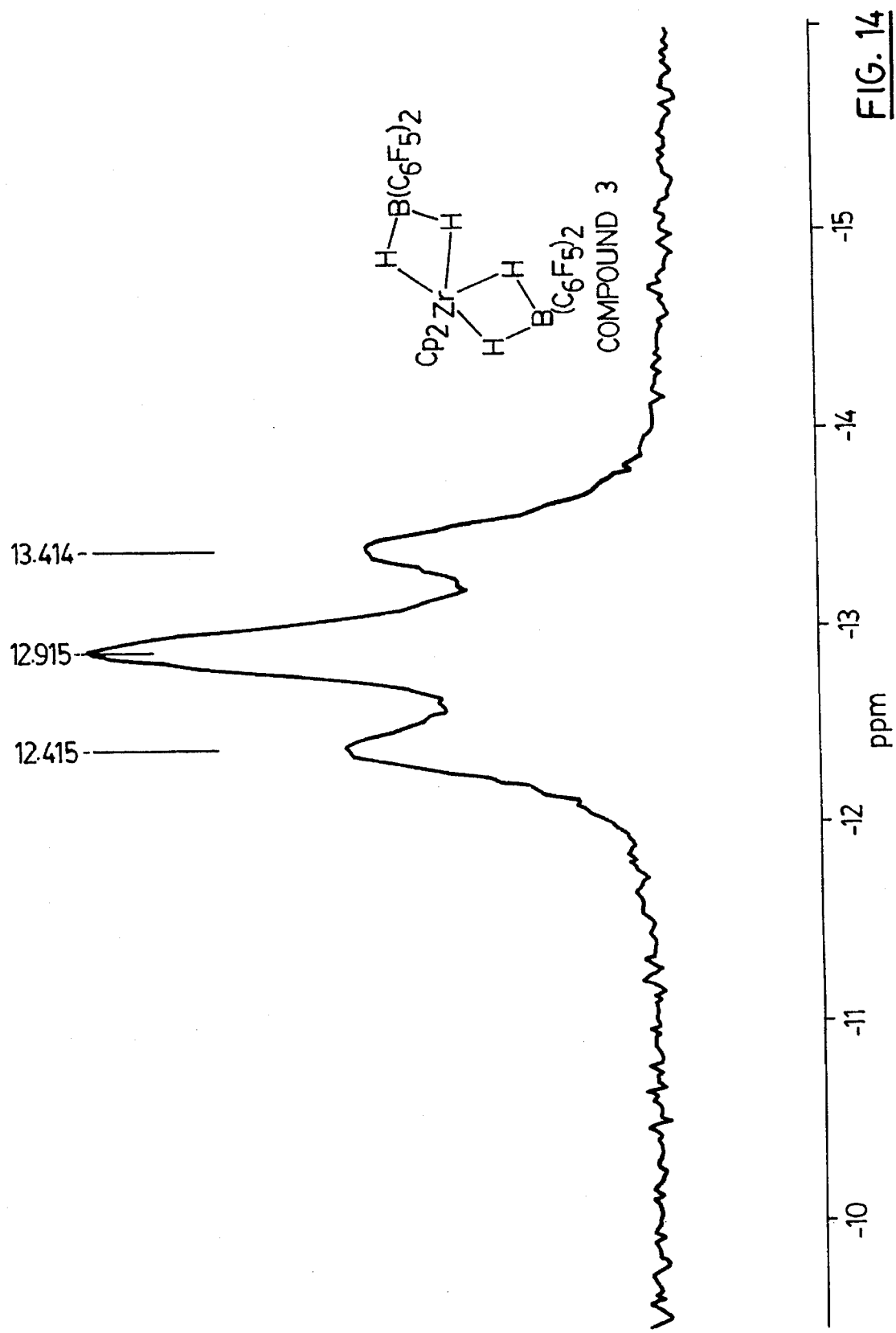
FIG. 14 shows the $^{11}B$ NMR spectrum of compound 3 in $C_6D_6$ solution.
Figure 15:
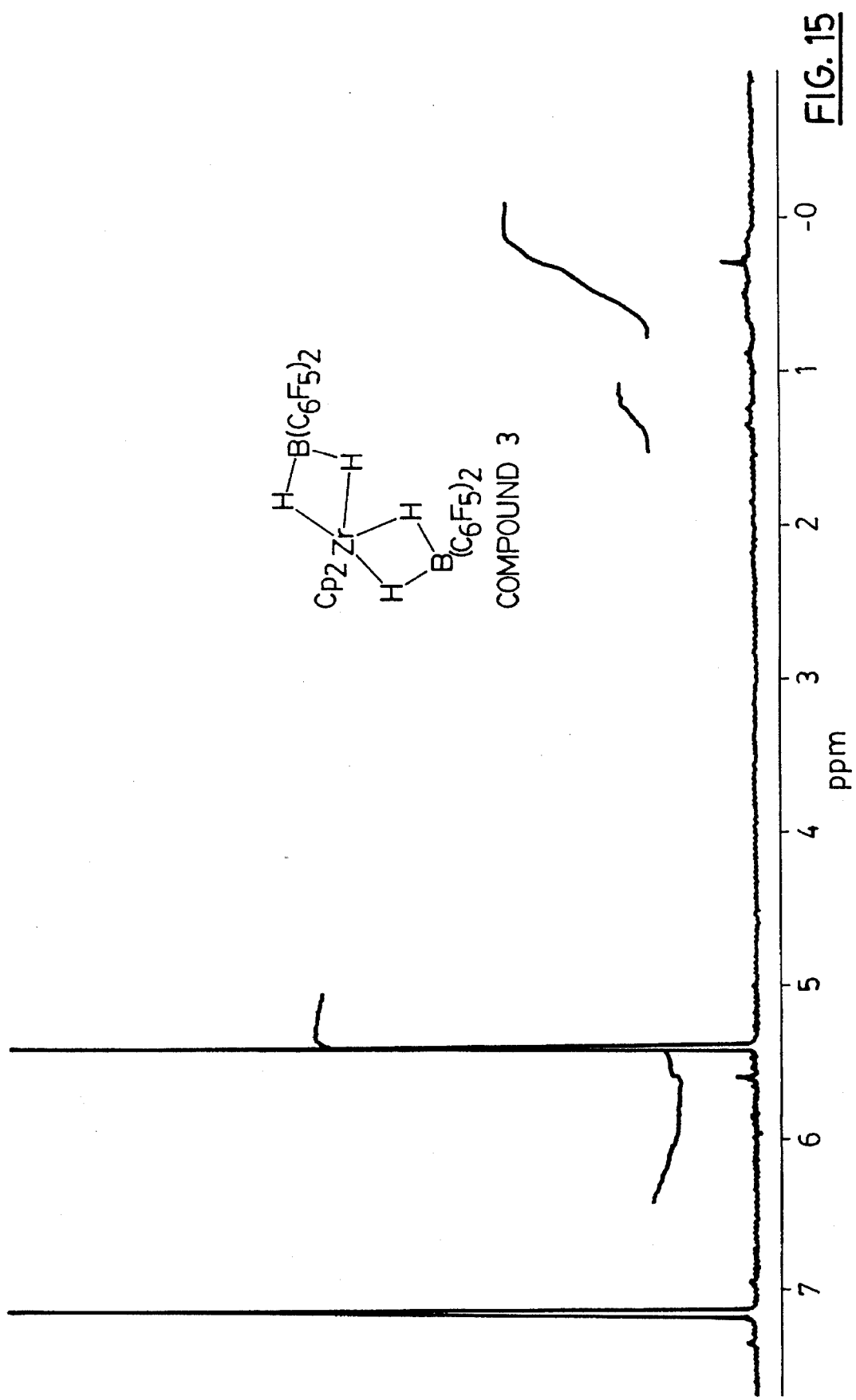
FIG. 15 shows the 400 MHz $^1H$ NMR spectrum of compound 3 in $C_6D_6$ solution.

The highly electrophilic borane reagent $B(C_6F_5)_2BH$, 1, forming the present invention has been found to be highly reactive towards zirconocene alkyls $Cp_2ZrR_2$, 2, (R=$CH_2SiMe_3$, 2a; $CH_2C_6H_5$, 2b; $CH_3$, 2c). As shown in reaction scheme IV in FIG. 12(a), addition of four equivalents of the borane reagent 1 to 2a and 2b ultimately led in each case to the bis-borohydride complex $Cp_2Zr[H_2B(C_6F_5)_2]_2$, 3. Referring to the infrared spectrum of 3 in FIG. 13, characteristic weak to medium intensity infra-red absorptions for the Zr-(μ-H)$_2$-B units at 2184, 2110 and 2028 cm$^{-1}$ (Zr-(μ-D)$_2$-B, 1597 cm$^{-1}$) and its synthesis via a separate route from $Cp_2ZrH_2$ and 1 (two equivalents) supported its formulation. Various NMR spectra of 3 are shown in FIGS. 14 and 15. Product 3 was sparingly soluble in aliphatic solvents and, as a solid, was remarkably stable to oxygen and moisture.

Figure 12A:
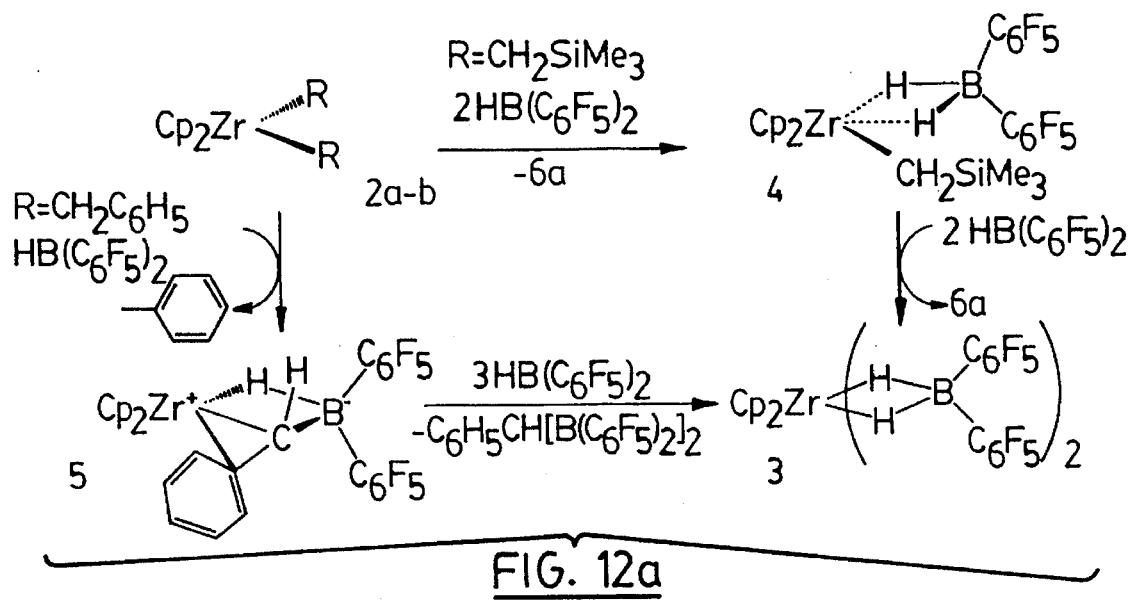
FIG. 12(a) illustrates reactions between Bis(pentafluorophenyl)borane with Bis-alkyl zirconocenes.
Figure 16:
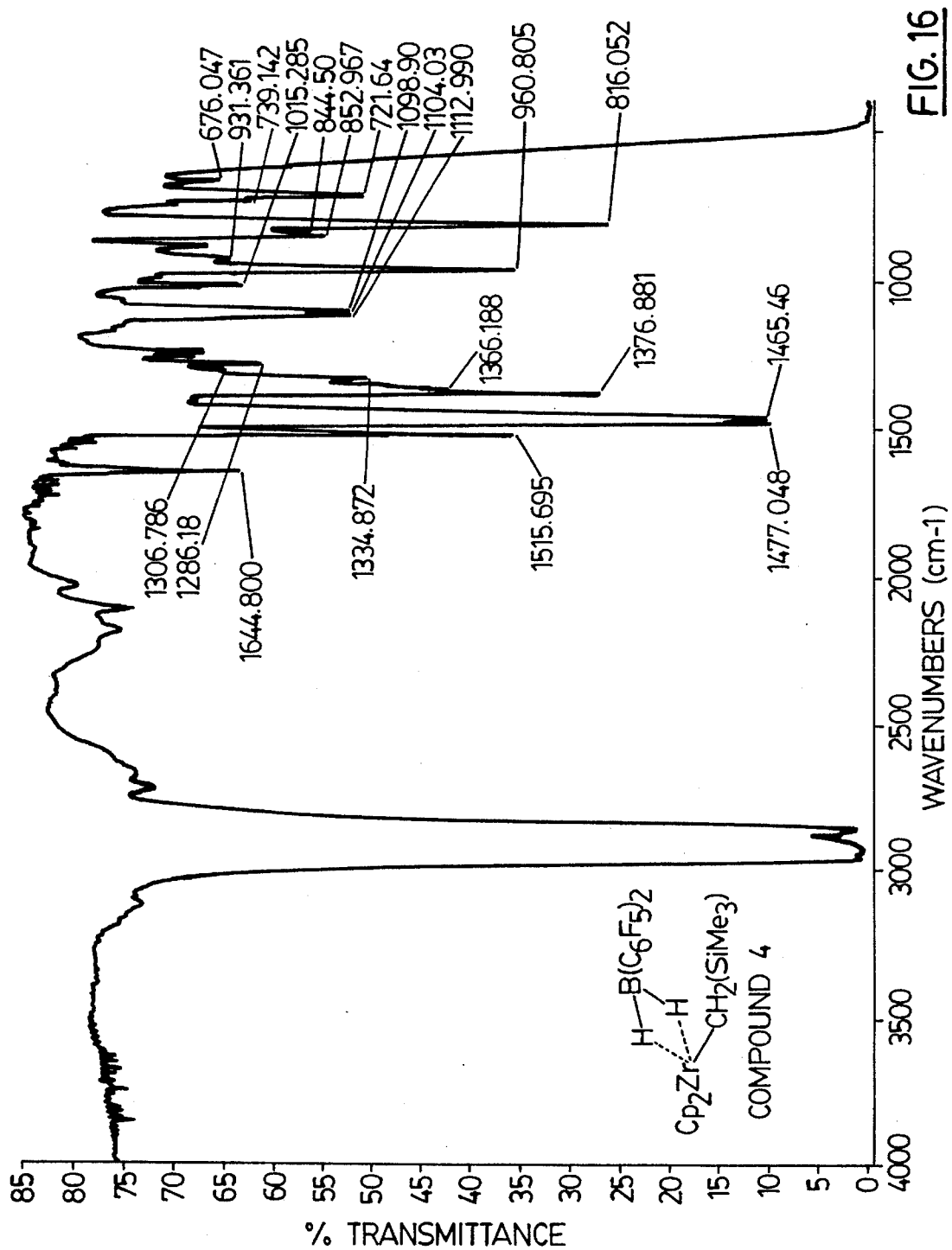
FIG. 16 shows the infrared spectrum of compound 4, as Nujol mull, described hereinafter.

Isolation of intermediates through limitation of the amount of 1 in these reactions was possible, and based on these observations, it is clear that two competing pathways to 3 were operative as shown in scheme IV in FIG. 12(a). The route followed was dependent on the nature of the alkyl group in 2. One path, illustrated by the reaction of 2a with 1, involved a two-step sequence of a hydride/alkyl exchange reaction followed by complexation of 1 with the resultant Zr-H moiety; this sequence occurred twice to yield 3. Thus, isolation of the intermediate $Cp_2Zr(CH_2SiMe_3)[H_2B(C_6F_5)_2]$, 4, was effected by treatment of 2a with two equivalents of 1. The infrared spectrum of intermediate 4 is shown in FIG. 16. Also produced was one equivalent of $Me_3SiCH_2B(C_6F_5)_2$, 6a (not shown but identified by separate synthesis via transmetallation using 2a and $ClB(C_6F_5)_2$); 4 was converted quantitatively to 3 and 6a upon addition of a further two equivalents of the borane reagent.

Figure 12B:
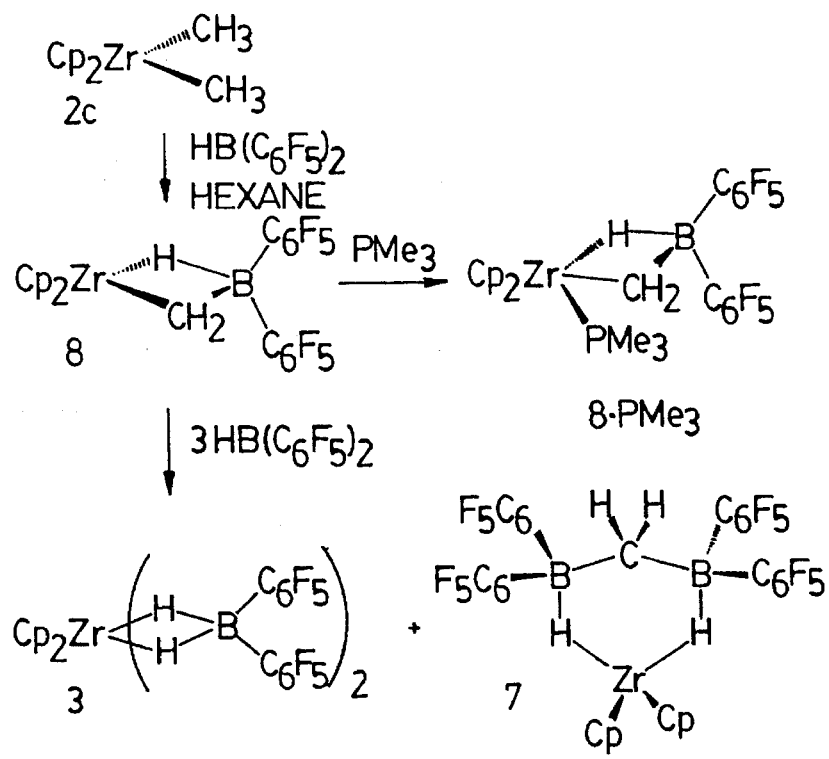
FIG. 12(b) illustrates more reactions between Bis(pentafluorophenyl)borane and dimethyl zirconocene.
Figure 17:
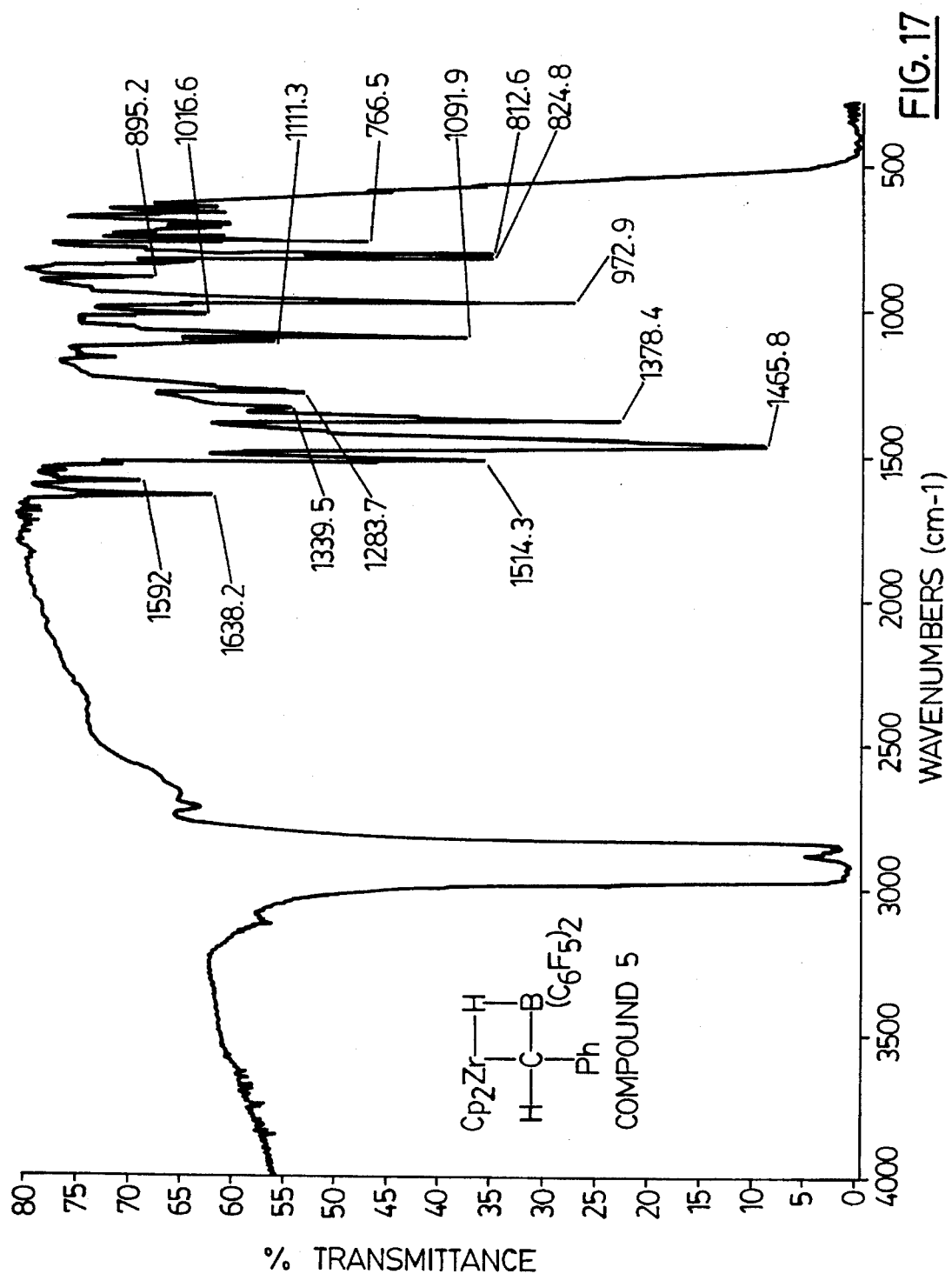
FIG. 17 shows the infrared spectrum of compound 5, as Nujol mull, described hereinafter.
Figure 18:
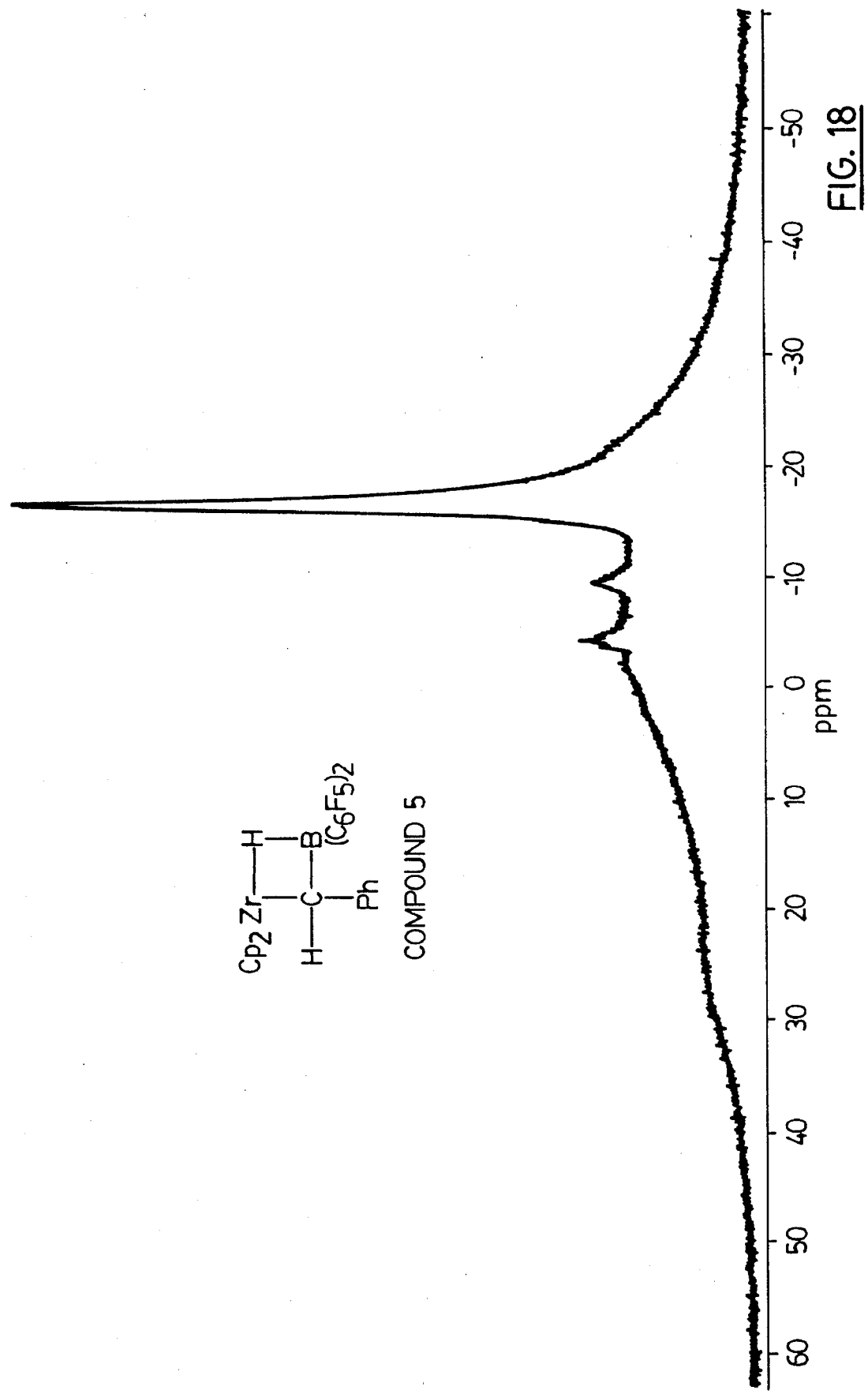
FIG. 18 shows the $^{11}B$ NMR spectrum of compound 5 in $C_6D_6$ solution.
Figure 19:
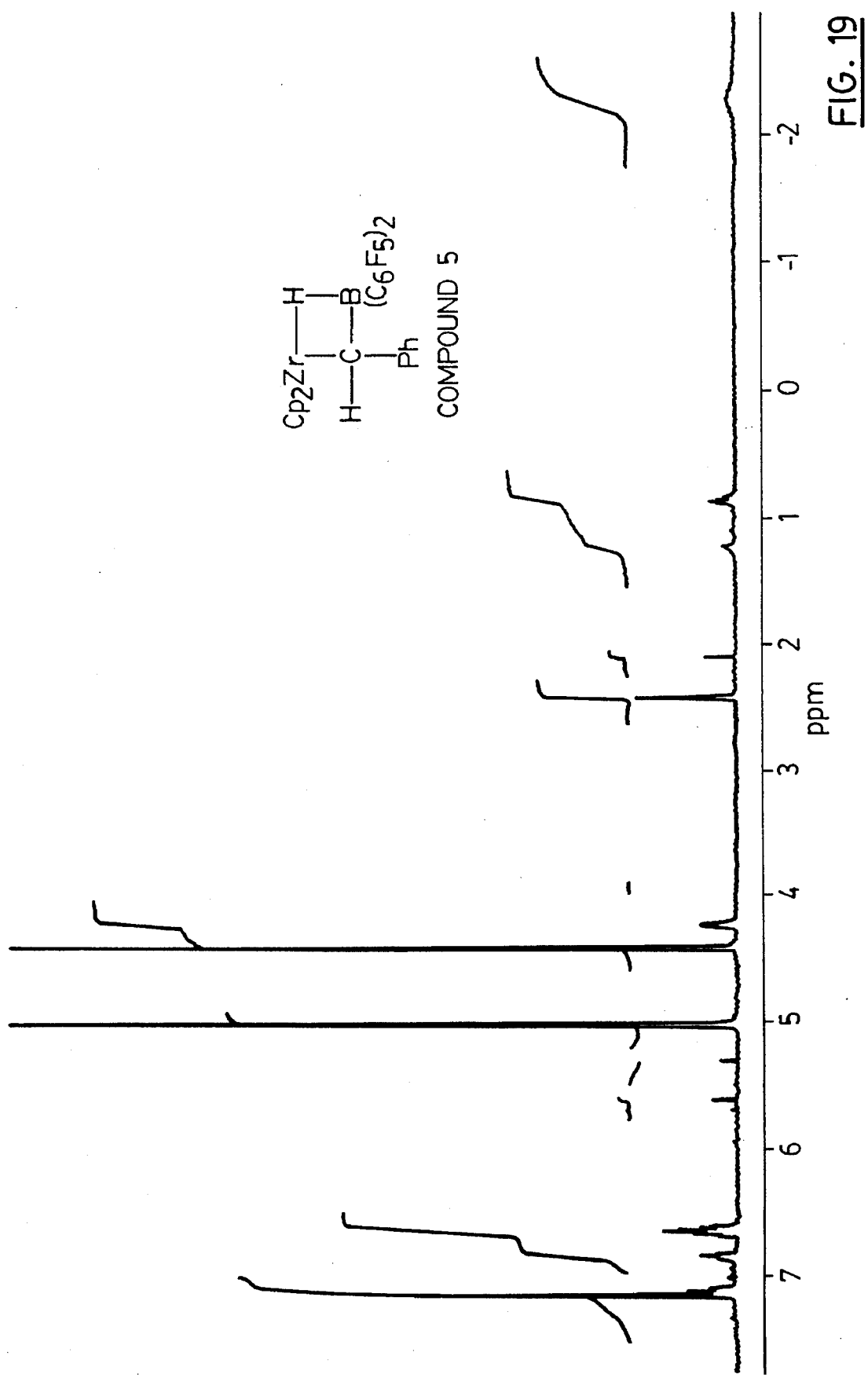
FIG. 19 shows the 400 MHz $^1H$ NMR spectrum of compound 5 in $C_6D_6$ solution.
Figure 20:
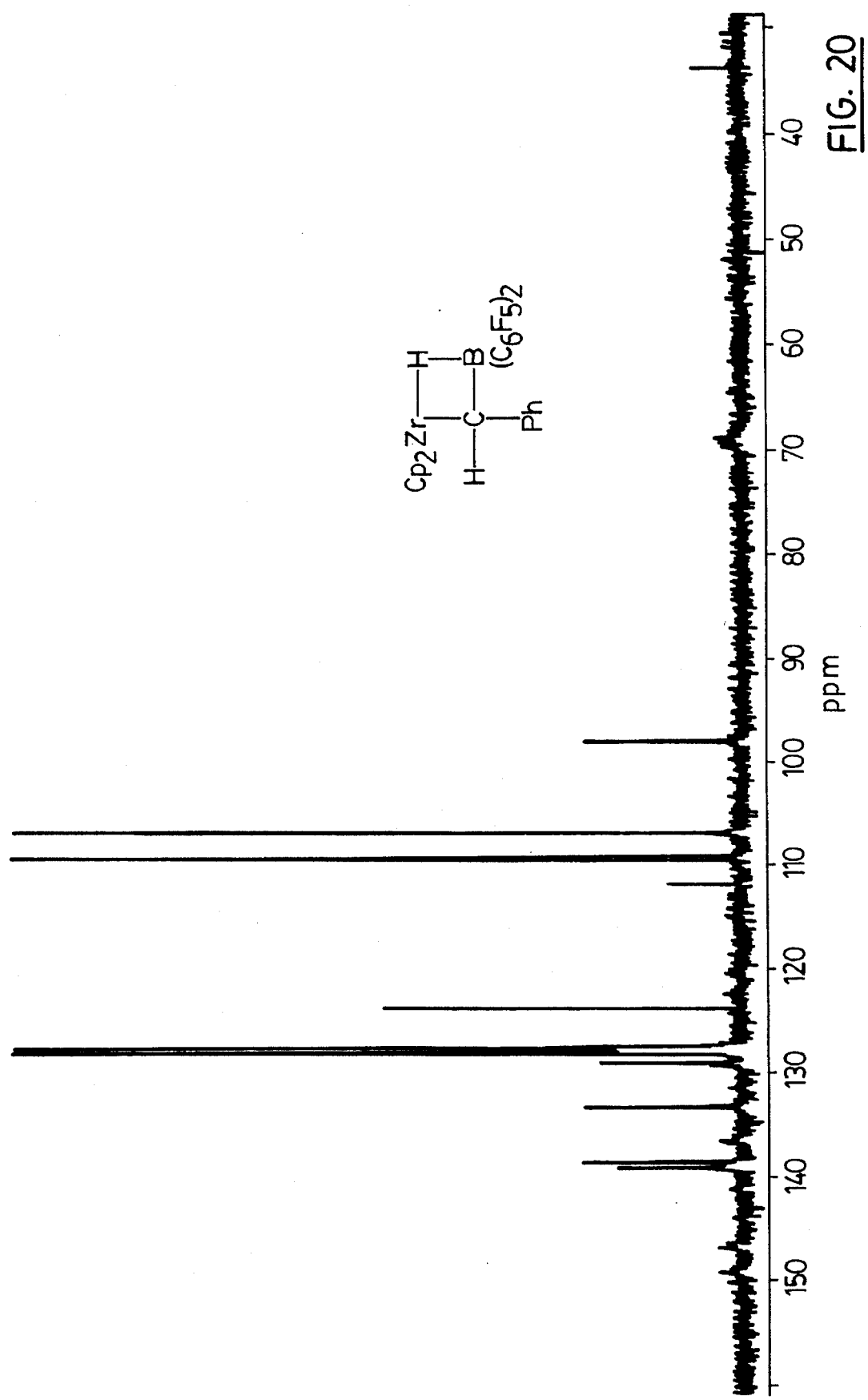
FIG. 20 shows the $^{13}C$ NMR spectrum of compound 5 in $C_6D_6$ solution.

The reaction of one equivalent of 1 with bis-benzyl zirconocene 2 b in hexanes produced $Cp_2Zr\{\eta^3\text{-}CH(C_6H_6)[(\mu\text{-}H)B(C_6F_5)_2]\}$, 5, and an equivalent of toluene (scheme V, FIG. 12(b)). The infrared spectrum of 5 is shown in FIG. 17. The chemical shift of the boron atom in the $^{11}$B NMR spectrum (−16.6 ppm, whh=190 Hz) of FIG. 18 was indicative of a four coordinate boron center as disclosed in R. G. Kidd, in *NMR of Newly Accessible Nuclei*, Vol. 2; Ed. P. Lasslo, Academic Press, New York, 1983. Multihapto bonding in the benzyl moiety was indicated by separate resonances in the $^1$H and $^{13}$C{$^1$H} NMR spectra (shown in FIGS. 19 and 20 respectively) for each of the inequivalent phenyl hydrogen and carbon atoms of the $C_6H_5$ unit. A broad resonance at −2.2 ppm in the $^1$H NMR spectrum, indicates the presence of a B-(μ-H)-M proton.

Figure 21:
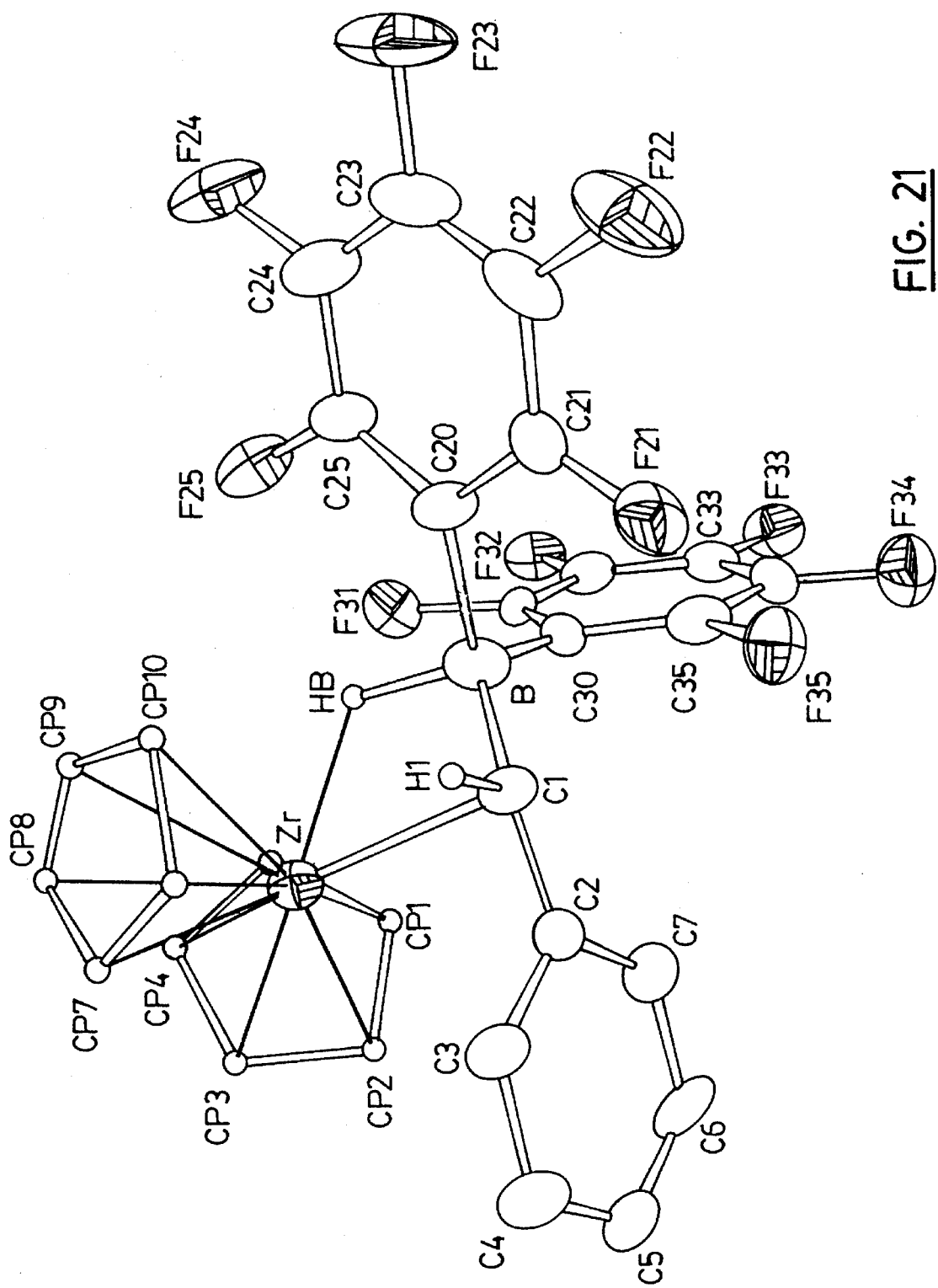
FIG. 21 shows the Oakridge Thermal Ellipsoid Plot (ORTEP) representation of the molecular structure of compound 5 described hereinafter.

The above spectroscopic data were consistent with compound 5's solid state structure shown in FIG. 21 as revealed by X-ray analysis. In general terms, 5 may be formulated as a zwitterionic zirconocene alkyl cation in which the borate counterion is attached covalently to the α-carbon of the alkyl ligand. The electron deficient zirconium center in 5 gains electron density from a μ-hydride ligand shared with the boron center and the multihapto benzyl unit. The Zr-C1 distance of 2.341(10)Å is typical of a normal Zr-$C_{alkyl}$ linkage 3b, see W. E. Hunter, D.C. Hrncir, R. Vann Bynum, R. A. Penttila, and J. L. Atwood, *Organometallics*, Vol. 2, p. 750, 1983. The Zr-C2 length of 2.583 Å, while longer, is within the range (2.627–2.648Å) of M-Cipso lengths observed in known h2 benzyl complexes of zirconium, see for example M. Bochmann, S. J. Lancaster, M. B. Hursthouse, K. M. Abdul Malik, *Organometallics*, Vol. 13, p. 2235, 1994. Although the Zr-C3 distance is longer still at 2.737 Å, the upfield shifts observed in the $^1$H (4.25 ppm) and $^{13}$C{$^1$H} (98.0 ppm) NMR spectra for C3 and its proton are suggestive of some interaction with the metal center.

The inventors speculate that the path leading to 5 involves an α abstraction process induced by complexation of 1 (A, see FIG. 11), in contrast with the substituent exchange chemistry observed when R= $CH_2SiMe_3$. Treatment of 5 with three equivalents of 1 gave 3 and a product containing neutral boron centers ($^{11}$B=74 ppm) and the benzyl unit from 5 assigned as $C_6H_5CH[B(C_6F_5)_2]_2$, likely formed via an exchange reaction between 5 and 1. The zirconium product of this exchange, $Cp_2ZrH_2$, while not observed, has been shown to react with borane 1to give 3 (vide supra).

Figure 22:
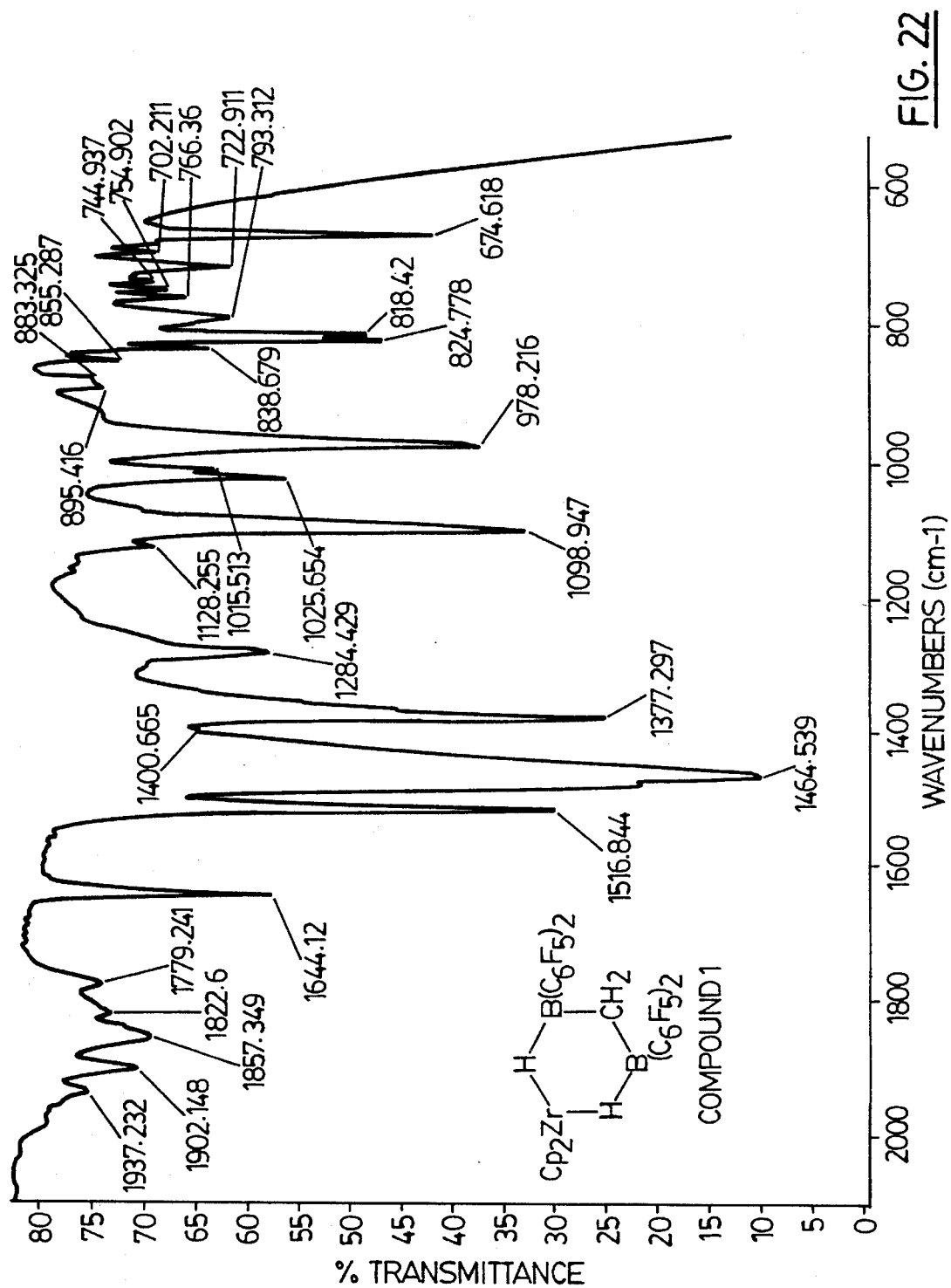
FIG. 22 shows the infrared spectrum of compound 7, as Nujol mull, described hereinafter.
Figure 23:
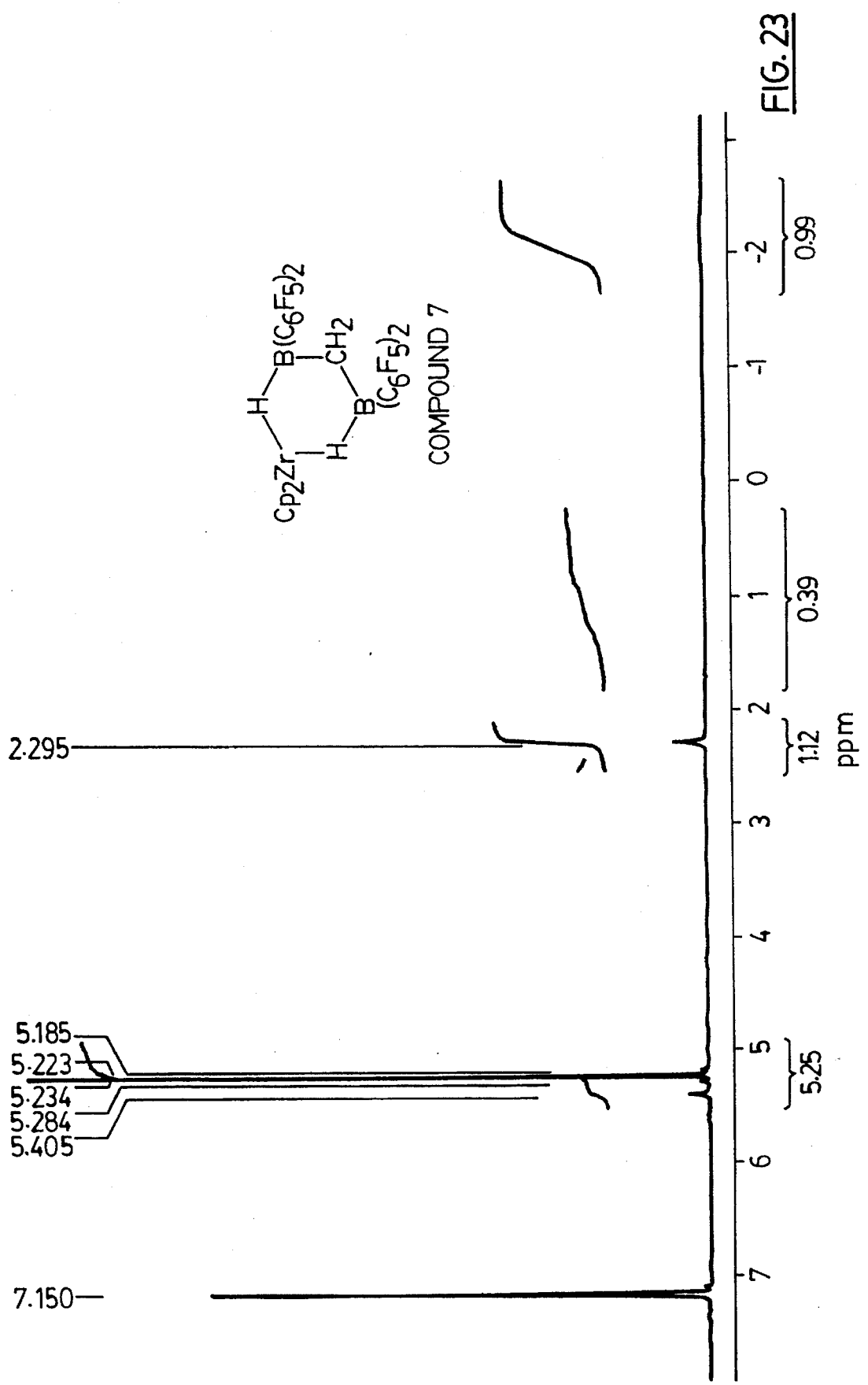
FIG. 23 shows the 400 MHz $^1H$ NMR spectrum of compound 7 in $C_6D_6$ solution.
Figure 24:
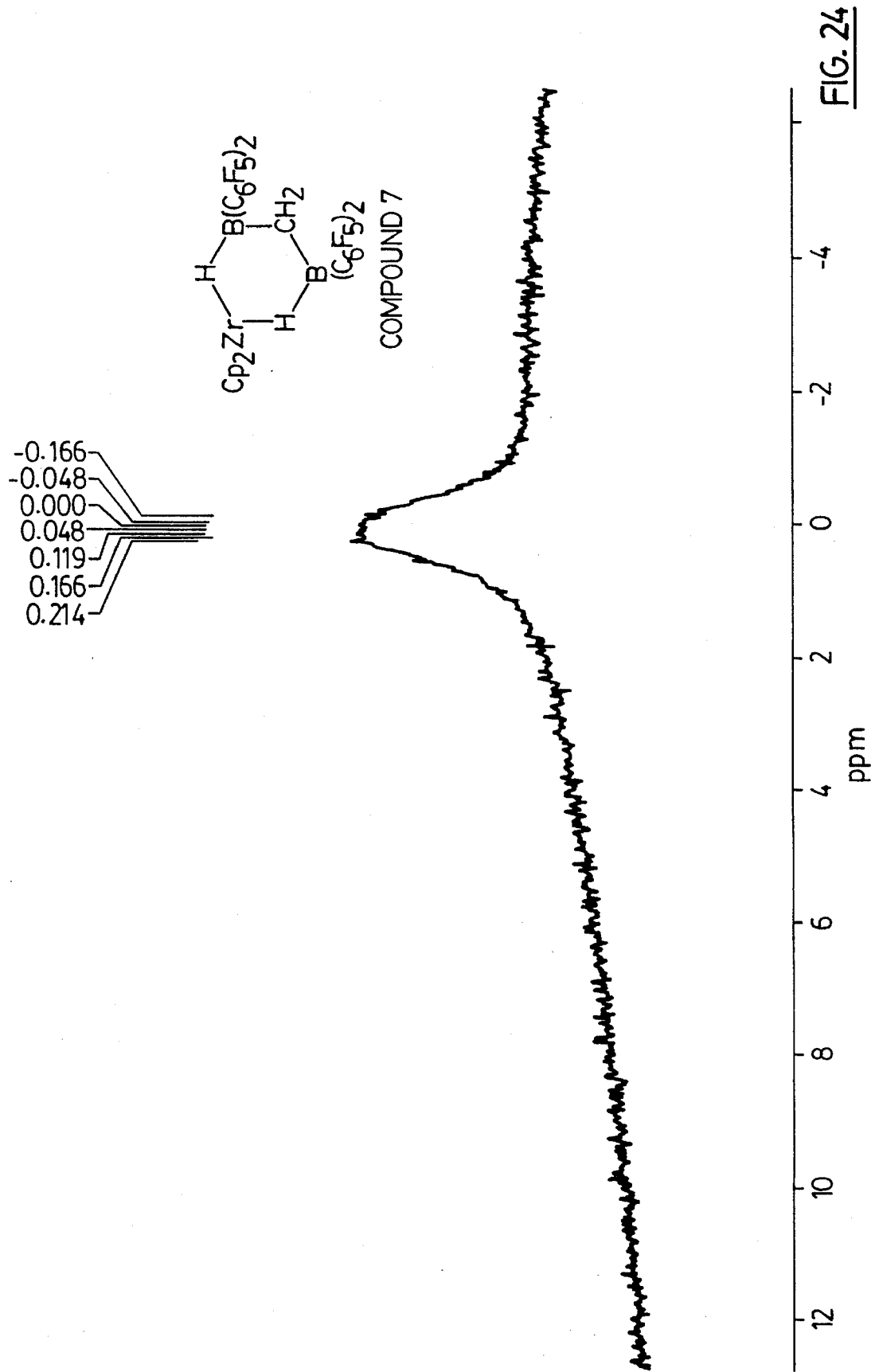
FIG. 24 shows the $^{11}B$ NMR spectrum of compound 7 in $C_6D_6$ solution.
Figure 25:
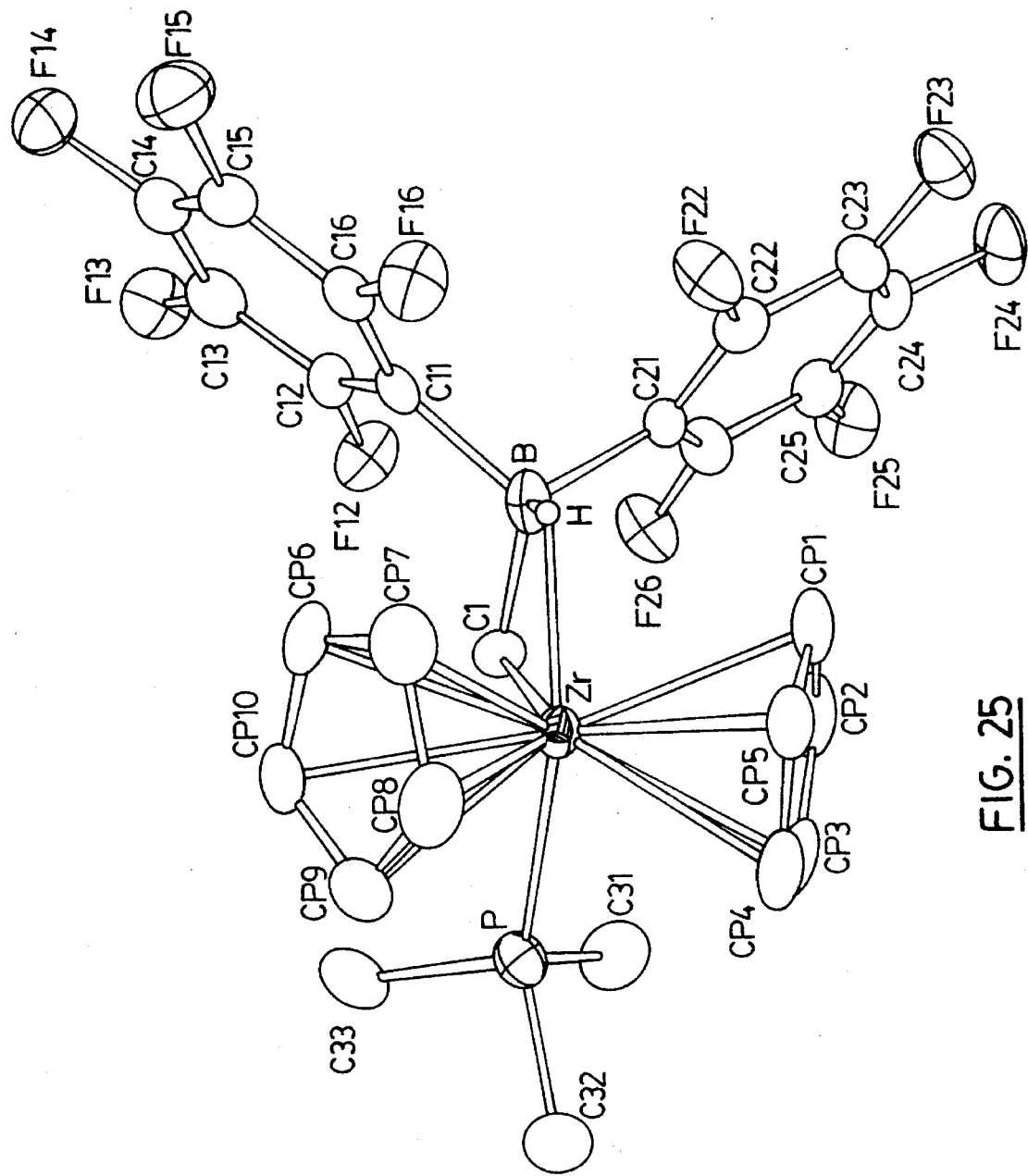
FIG. 25 is the ORTEP representation of the molecular structure of the trimethylphosphine adduct of compound 8 described hereinafter.

Referring to reaction scheme V in FIG. 12(b), the reaction of 1 with dimethyl zirconocene 2c was more complex and illustrates the delicate balance between the two available reaction coordinates described above. Treatment of 2c with four equivalents of 1 gave a and a new compound, 7, in a≈1:2 ratio (Equation 1). The infrared, $^1$H and $^{11}$B NMR spectra are displayed in FIGS. 22 to 24 respectively. Gas evolution was observed and methane was detected by $^1$H NMR, along with $CH_3B(C_6F_5)_2$, indicating that both pathways discussed above were accessible in this reaction. In this system, a arose from the exchange/complexation sequence, while 7, formulated as an adduct between $Cp_2ZrH_2$ and the byproduct $CH_2[B(C_6F_5)_2]_2$, was the end product of the α-abstraction pathway. When 2c was reacted with 1 in hexanes, a compound structurally analogous to 5 was isolated in excellent yield. This compound, 8, was somewhat thermally unstable but was characterized as its $PMe_3$ adduct, 8.$PMe_3$, the structure of which is shown in FIG. 25.

Those skilled in the art will appreciate that complex 5 will exhibit interesting properties as an olefin polymerization catalyst because any polymerization propagation may lead to physical separation of the ion pair. Preliminary experiments suggest that 5 is moderately active towards ethylene polymerization.

TABLE 1

The Hydroboration of Simple Olefins and Alkynes Using Bis-(Pentafluorophenyl)borane.[a]

| Entry | Substrate | Product (1 equivalent 1) | Product (2 equivalents 1) |
|---|---|---|---|
| 1 | (alkene structure) | H, $B(C_6F_5)_2$ (structure) | |

TABLE 1-continued

The Hydroboration of Simple Olefins and Alkynes Using Bis-(Pentafluorophenyl)borane.[a]

| Entry | Substrate | Product (1 equivalent 1) | Product (2 equivalents 1) |
|---|---|---|---|
| 2[b] | (cyclopentene with methyl) | cyclopentyl-B(C$_6$F$_5$)$_2$ with H | |
| 3[b] | (cyclohexene with methyl) | cyclohexyl-B(C$_6$F$_5$)$_2$ with H | |
| 4[c] | allyl-D | (C$_6$F$_5$)$_2$B-CH(D)-CH(D)- | |
| 5[d] | styrene | PhCH$_2$CH$_2$-B(C$_6$F$_5$)$_2$ | |
| 6 | HC≡CH | H, B(C$_6$F$_5$)$_2$ vinyl | No reaction |
| 7[b] | phenylacetylene | PhCH=CH-B(C$_6$F$_5$)$_2$ | PhCH(B(C$_6$F$_5$)$_2$)CH$_2$-B(C$_6$F$_5$)$_2$ |
| 8[b],[e] | Si-C≡CH | Si-CH=CH-B(C$_6$F$_5$)$_2$ | Si-CH(B(C$_6$F$_5$)$_2$)CH$_2$-B(C$_6$F$_5$)$_2$ |
| 9[f] | Si-CH=CH$_2$ | Si-CH(B(C$_6$F$_5$)$_2$)CH$_3$ | |

[a]Yields of these reactions were 100% by $^1$H NMR.
[b]Reaction > 98% regioselective.
[c]d$_1$ − 1 was used in this reaction.
[d]Small amounts (≈ 4%) of the other regioisomer were detected.
[e]The second hydroboration initially produced a mixture of regioisomers which converted quantitatively to the thermodynamic product shown.
[f]A thermodynamic mixture of isomers was observed (85:15); favored isomer shown.

Therefore what is claimed is:

1. A compound having the formula $[(C_6R_5)_2BH]_n$, wherein n is selected from the group consisting of 1 and 2, and wherein R is selected from the group consisting of fluorine (F), hydrogen (H), (trifluoromethyl) (CF$_3$) groups, and combinations thereof but not consisting entirely of H.

2. The compound according to claim 1 wherein R is F.

3. The compound according to claim 2 characterized by infrared absorption bands at about 1395 cm$^{-1}$ and at about 1550 cm$^{-1}$.

4. The compound according to claim 2 characterized by $^{19}$F NMR major peaks at −134.8 (2F), −148.0 (1 F) due to a dimer species, n=2, and minor peaks at −160.7 (2F), −130.5 (2F), −143.4 (1F) and −161.7 (2F) due to monomer species, n=1.

5. The compound according to claim 1 wherein $[(C_6R_5)_2BH]_n$ is $[[3,5$ -$(CR'_3)_2C_6R''_3]_2BH]_n$, and R' and R" are selected from the group consisting of F and H.

6. The compound according to claim 5 wherein R' is F and R" is H.

7. A method of producing $[(C_6F_5)_2BH]_2$, of the steps of:
   providing an amount of $ClB(C_6F_5)_2$;
   mixing said $ClB(C_6F_5)_2$ with a source of hydride in a temperature range from about −78° C. to about room temperature to produce a solution in which a precipitate comprising $[(C_6F_5)_2BH]_2$ is formed; and isolating said $[(C_6F_5)_2BH]_2$ from said solution.

8. The method according to claim 7 wherein said source of hydride is selected from the group consisting of $R_3MH$ and $R_2(Cl)MH$, wherein R is selected from the group consisting of alkyl and aryl functional groups and M is selected from the group consisting of Si, Ge and Sn.

9. The method according to claim 7 wherein said source of hydride is selected from the group consisting of $Cp_2MH_2$ and $Cp_2M(Cl)H$, wherein Cp is cyclopentadienyl and M is selected from the group consisting of Ti, Zr and Hf.

10. The method according to claim 7 wherein said source of hydride is a metal hydride selected from the group consisting of Group 4 and Group 14 metal hydrides.

11. The method according to claim 7 wherein said source of hydride is selected from the group consisting of $(Cl)H-SiMe_2$, $[Cp_2Zr(Cl)H]_n$ and $Bu_3SnH$.

12. A method of hydroborating alkenes by reaction with $(C_6F_5)_2BH$, comprising:

providing a quantity of $[(C_6F_5)_2BH]_2$ and a quantity of an alkene; and mixing said quantity of $[(C_6F_5)_2BH]_2$ with a dry aromatic organic solvent to produce a suspension comprising an equilibrium mixture of $[(C_6F_5)_2BH]_2$ and $(C_6F_5)_2BH$ and mixing therewith said quantity of said alkene, such that said alkene reacts with said $(C_6F_5)_2BH$ to undergo hydroboration.

13. The method according to claim 12 wherein said alkene and said dry organic solvent are reacted together in the temperature range from about −78° C. to about room temperature.

14. The method according to claim 13 wherein said alkene is $R^1R^2C=CR^3R^4$, wherein $R^1$, $R^2$, $R^3$ and $R^4$ are selected from the group consisting of H, and alkyl and aryl functional groups.

15. A method of hydroborating alkynes by reaction with $(C_6F_5)_2BH$, comprising:

providing a quantity of $[(C_6F_5)_2BH]_2$ and a quantity of an alkyne; and mixing said quantity of $[(C_6F_5)_2BH]_2$ with a dry aromatic organic solvent to produce a suspension comprising an equilibrium mixture of $[(C_6F_5)_2BH]_2$ and $(C_6F_5)_2BH$ and mixing therewith said quantity of said alkyne, such that said alkyne reacts with said $(C_6F_5)_2BH$ to undergo hydroboration.

16. The method according to claim 15 wherein said alkyne is dried, and said alkyne and said dry organic solvent are reacted together in a temperature range from about −78° C. to about room temperature under an inert atmosphere.

17. The method according to claim 15 wherein said alkyne is $R^1CCR^2$, wherein $R^1$ and $R^2$ are selected from the group consisting of H, and alkyl and aryl functional groups.

18. A compound having the formula $Cp_2Zr\{R'''[(\mu-H)B(C_6F_5)_2]\}$ wherein Cp is cyclopentadienyl and $R'''$ is selected from the group consisting of $CH_2$ and $(\eta^3-CH(C_6H_5))$.

19. A method of producing chelating bis borane co-catalysts by hydroboration of terminal alkynes by reaction with $(C_6F_5)_2BH$, comprising:

providing an amount of a terminal alkyne having a formula $RC\equiv CH$ wherein R is selected from the group consisting of tertiary butyl, and phenyl and alkyl organic functional groups; and reacting said terminal alkyne with an effective amount of $(C_6F_5)_2BH$ to cause said terminal alkyne to undergo hydroboration to produce chelating bis borane co-catalysts having a formula $RCH_2CH[B(C_6F_5)_2]_2$.

\* \* \* \* \*